US010893955B2

(12) United States Patent
Goodchild et al.

(10) Patent No.: US 10,893,955 B2
(45) Date of Patent: Jan. 19, 2021

(54) NON-SYMMETRICAL INSERT SENSING SYSTEM AND METHOD THEREFOR

(71) Applicant: Orthosensor Inc., Dania Beach, FL (US)

(72) Inventors: Gordon Goodchild, Coral Springs, FL (US); Ryan Ortiz, Miramar, FL (US); Andrew Chase, Chandler, AZ (US)

(73) Assignee: Orthosensor Inc., Dania Beach, FL (US)

( * ) Notice: Subject to any disclaimer, the term of this patent is extended or adjusted under 35 U.S.C. 154(b) by 87 days.

(21) Appl. No.: 16/122,628

(22) Filed: Sep. 5, 2018

(65) Prior Publication Data

US 2019/0076272 A1 Mar. 14, 2019

Related U.S. Application Data

(60) Provisional application No. 62/558,699, filed on Sep. 14, 2017, provisional application No. 62/558,720, (Continued)

(51) Int. Cl.
*A61F 2/46* (2006.01)
*A61B 5/00* (2006.01)
(Continued)

(52) U.S. Cl.
CPC ............ *A61F 2/468* (2013.01); *A61B 5/4528* (2013.01); *A61B 5/4585* (2013.01); *A61B 5/4851* (2013.01); *A61B 5/6847* (2013.01); *A61B 5/6878* (2013.01); *A61B 17/025* (2013.01); *A61B 90/06* (2016.02); *A61F 2/38* (2013.01); *A61F 2/4657* (2013.01); *A61F 2/4684* (2013.01); *A61B 5/1036* (2013.01); *A61B 5/4504* (2013.01); *A61B 34/10* (2016.02); *A61B 34/20* (2016.02); *A61B 34/25* (2016.02); *A61B 2017/0268* (2013.01); *A61B 2034/2048* (2016.02); *A61B 2034/256* (2016.02); *A61B 2090/061* (2016.02); *A61B 2090/062* (2016.02);
(Continued)

(58) Field of Classification Search
CPC ... A61B 5/1036; A61B 5/4504; A61B 5/4528; A61B 5/4585; A61B 5/4851; A61B 5/6878; A61B 17/025; A61B 2017/0268; A61F 2/38; A61F 2/4657; A61F 2002/4666; A61F 2/468; A61F 2/4684
See application file for complete search history.

(56) References Cited

U.S. PATENT DOCUMENTS 3,727,616 A 4/1973 Lenzkes
4,066,082 A 1/1978 Arcan et al.
(Continued)

*Primary Examiner* — Larry E Waggle, Jr.

(57) ABSTRACT

An orthopedic system to monitor a parameter related to the muscular-skeletal system is disclosed. The orthopedic system includes electronic circuitry, at least one sensor, and a computer to receive measurement data in real-time. The orthopedic system comprises a first plurality of shims of a first type, a second plurality of a second type, a measurement module, and the computer. The measurement module houses the electronic circuitry and at least one sensor. The measurement module is adapted to be used with the first plurality of shims and the second plurality of shims. The measurement module has a medial surface that differs from a lateral surface by shape, size, or contour.

20 Claims, 11 Drawing Sheets

Related U.S. Application Data filed on Sep. 14, 2017, provisional application No. 62/558,704, filed on Sep. 14, 2017.

(51) Int. Cl.
*A61B 90/00* (2016.01)
*A61B 34/10* (2016.01)
*A61B 17/02* (2006.01)
*A61F 2/38* (2006.01)
*A61B 34/00* (2016.01)
*A61B 34/20* (2016.01)
*A61B 5/103* (2006.01)

(52) U.S. Cl.
CPC ... *A61B 2090/064* (2016.02); *A61B 2090/065* (2016.02); *A61F 2002/4632* (2013.01); *A61F 2002/4666* (2013.01)

(56) References Cited

U.S. PATENT DOCUMENTS

| | | |
|---|---|---|
| 4,092,597 A | 5/1978 | Place |
| 4,127,110 A | 11/1978 | Bullara |
| 4,277,758 A | 7/1981 | Mishiro |
| 4,480,485 A | 11/1984 | Bradshaw et al. |
| 4,731,762 A | 3/1988 | Hanks |
| 4,764,804 A | 8/1988 | Sahara et al. |
| 4,857,893 A | 8/1989 | Carrol |
| 4,899,761 A | 2/1990 | Brown et al. |
| 4,902,958 A | 2/1990 | Cook, II |
| 4,920,279 A | 4/1990 | Charlet et al. |
| 4,983,533 A | 1/1991 | Go |
| 4,986,281 A | 1/1991 | Preves et al. |
| 5,042,489 A | 8/1991 | Weiner et al. |
| 5,119,676 A | 6/1992 | Bower et al. |
| 5,456,724 A | 10/1995 | Yen et al. |
| 5,470,354 A | 11/1995 | Hershberger et al. |
| 5,569,260 A | 10/1996 | Petersen |
| 5,650,571 A | 7/1997 | Freud et al. |
| 5,669,914 A | 9/1997 | Eckhoff |
| 5,683,396 A | 11/1997 | Tokish et al. |
| 5,688,279 A | 11/1997 | McNulty et al. |
| 5,733,292 A * | 3/1998 | Gustilo ............... A61B 17/025 606/86 R |
| 5,871,018 A | 2/1999 | Delp et al. |
| 5,879,298 A | 3/1999 | Drobnitzky et al. |
| 5,900,592 A | 5/1999 | Sohns et al. |
| 6,072,784 A | 6/2000 | Agrawal et al. |
| 6,092,530 A | 7/2000 | Weissman et al. |
| 6,115,636 A | 9/2000 | Ryan |
| 6,165,142 A | 12/2000 | Bar |
| 6,184,651 B1 | 2/2001 | Fernandez et al. |
| 6,245,109 B1 | 6/2001 | Mendes et al. |
| 6,385,475 B1 | 5/2002 | Cinquin et al. |
| 6,425,920 B1 | 7/2002 | Hamada |
| 6,429,585 B1 | 8/2002 | Kitazume et al. |
| 6,443,891 B1 | 9/2002 | Grevious |
| 6,447,448 B1 | 9/2002 | Ishikawa et al. |
| 6,580,947 B1 | 6/2003 | Thompson |
| 6,583,630 B2 | 6/2003 | Mendes et al. |
| 6,621,278 B2 | 9/2003 | Ariav |
| 6,739,068 B1 | 5/2004 | Rinner |
| 6,796,988 B2 | 9/2004 | Melkent et al. |
| 6,856,141 B2 | 2/2005 | Ariav |
| 6,859,661 B2 | 2/2005 | Tuke |
| 6,993,393 B2 | 1/2006 | Von Arx et al. |
| 7,080,554 B2 | 7/2006 | Ariav et al. |
| 7,097,662 B2 | 8/2006 | Evans, III et al. |
| 7,141,020 B2 | 11/2006 | Poland et al. |
| 7,153,281 B2 | 12/2006 | Holmes |
| 7,173,749 B2 | 2/2007 | Maleki et al. |
| 7,195,645 B2 | 3/2007 | Disilvestro et al. |
| 7,195,654 B2 | 3/2007 | Jackson et al. |
| 7,215,599 B2 | 5/2007 | Nishimori et al. |
| 7,256,695 B2 | 8/2007 | Hamel et al. |
| 7,266,989 B2 | 9/2007 | Ariav |
| 7,283,867 B2 | 10/2007 | Strother et al. |
| 7,344,493 B2 | 3/2008 | Sonnenschein et al. |
| 7,347,817 B2 | 3/2008 | Glukhovsky et al. |
| 7,378,916 B2 | 5/2008 | Oita et al. |
| 7,384,403 B2 | 6/2008 | Sherman |
| 7,396,336 B2 | 7/2008 | Orszulak et al. |
| 7,412,897 B2 | 8/2008 | Crottet et al. |
| 7,432,788 B2 | 10/2008 | Glukh et al. |
| 7,442,196 B2 | 10/2008 | Fisher et al. |
| 7,454,972 B2 | 11/2008 | Heyman et al. |
| 7,477,926 B2 | 1/2009 | McCombs |
| 7,481,780 B2 | 1/2009 | De Guise et al. |
| 7,519,422 B2 | 4/2009 | Lippert et al. |
| 7,559,951 B2 | 7/2009 | DiSilvestro et al. |
| 7,575,602 B2 | 8/2009 | Amirouche |
| 7,578,821 B2 | 8/2009 | Fisher et al. |
| 7,615,055 B2 | 11/2009 | DiSilvestro |
| 7,630,774 B2 | 12/2009 | Karni et al. |
| 7,632,283 B2 | 12/2009 | Heldreth |
| 7,639,006 B2 | 12/2009 | Deffeyes |
| 7,643,862 B2 | 1/2010 | Schoenfeld |
| 7,668,201 B2 | 2/2010 | Sharony et al. |
| 7,672,726 B2 | 3/2010 | Ginggen |
| 7,725,288 B2 | 5/2010 | Boillot |
| 7,769,947 B2 | 8/2010 | Ranganathan et al. |
| 7,819,826 B2 | 10/2010 | Diederich et al. |
| 7,918,887 B2 | 4/2011 | Roche |
| 8,000,926 B2 | 8/2011 | Roche |
| 8,070,695 B2 | 12/2011 | Gupta et al. |
| 8,098,544 B2 | 1/2012 | Roche |
| 8,099,168 B2 | 1/2012 | Roche |
| 8,141,437 B2 | 3/2012 | Amirouche et al. |
| 8,167,823 B2 | 5/2012 | Nycz |
| 8,169,185 B2 | 5/2012 | Partovi et al. |
| 8,197,549 B2 | 6/2012 | Amirouche et al. |
| 8,211,041 B2 | 7/2012 | Fisher et al. |
| 8,245,583 B2 | 8/2012 | Stein |
| 8,270,253 B1 | 9/2012 | Roche |
| 8,295,920 B2 | 10/2012 | Bouton et al. |
| 8,372,147 B2 | 2/2013 | Roche |
| 8,372,153 B2 | 2/2013 | Roche |
| 8,421,479 B2 | 4/2013 | Stein |
| 8,421,642 B1 | 4/2013 | Roche |
| 8,427,176 B2 | 4/2013 | Stein |
| 8,444,654 B2 | 5/2013 | Roche |
| 8,449,556 B2 | 5/2013 | Roche |
| 8,494,805 B2 | 7/2013 | Roche |
| 8,498,711 B2 | 7/2013 | Roche |
| 8,516,884 B2 | 8/2013 | Stein et al. |
| 8,516,907 B2 | 8/2013 | Stein et al. |
| 8,659,661 B2 | 2/2014 | Frank et al. |
| 8,668,646 B2 | 3/2014 | Stein et al. |
| 8,679,186 B2 | 3/2014 | Stein et al. |
| 8,689,647 B2 | 4/2014 | Stein |
| 8,696,756 B2 | 4/2014 | Stein et al. |
| 8,701,484 B2 | 4/2014 | Stein et al. |
| 8,707,782 B2 | 4/2014 | Stein et al. |
| 8,720,270 B2 | 5/2014 | Stein et al. |
| 8,746,062 B2 | 6/2014 | Stein et al. |
| 8,826,733 B2 | 9/2014 | Stein et al. |
| 8,926,530 B2 | 1/2015 | Stein et al. |
| 8,979,758 B2 | 3/2015 | Stein et al. |
| 9,119,733 B2 | 9/2015 | Stein et al. |
| 9,125,627 B2 | 9/2015 | Stein |
| 9,161,717 B2 | 10/2015 | Stein et al. |
| 9,226,694 B2 | 1/2016 | Stein et al. |
| 9,259,172 B2 | 2/2016 | Stein et al. |
| 9,259,179 B2 | 2/2016 | Stein |
| 9,265,447 B2 | 2/2016 | Stein et al. |
| 9,265,462 B2 | 2/2016 | McIntosh et al. |
| 9,271,675 B2 | 3/2016 | Stein et al. |
| 9,289,163 B2 | 3/2016 | Stein et al. |
| 9,301,720 B2 | 4/2016 | Stein |
| 9,332,943 B2 | 5/2016 | Stein et al. |
| 9,339,212 B2 | 5/2016 | Stein et al. |
| 9,345,449 B2 | 5/2016 | Stein et al. |
| 9,345,492 B2 | 5/2016 | Stein et al. |
| 9,351,782 B2 | 5/2016 | Stein et al. |

(56) References Cited

U.S. PATENT DOCUMENTS

| | | | |
|---|---|---|---|
| 9,357,964 B2 | 6/2016 | Stein et al. | |
| 9,358,136 B2 | 6/2016 | Stein et al. | |
| 9,408,557 B2 | 8/2016 | Stein et al. | |
| 9,456,769 B2 | 10/2016 | Stein et al. | |
| 9,462,964 B2 | 10/2016 | Stein et al. | |
| 9,492,115 B2 | 11/2016 | Stein et al. | |
| 9,492,116 B2 | 11/2016 | Stein | |
| 9,492,119 B2 | 11/2016 | Stein et al. | |
| 9,492,238 B2 | 11/2016 | Stein et al. | |
| 9,492,290 B2 * | 11/2016 | Claypool | A61F 2/4657 |
| 9,566,020 B2 | 2/2017 | Stein et al. | |
| 9,615,887 B2 | 4/2017 | Stein et al. | |
| 9,622,701 B2 | 4/2017 | Stein et al. | |
| 9,642,571 B2 | 5/2017 | McIntosh et al. | |
| 9,642,676 B2 | 5/2017 | Stein et al. | |
| 9,820,678 B2 | 11/2017 | Stein et al. | |
| 9,844,335 B2 | 12/2017 | Stein et al. | |
| 10,004,449 B2 | 6/2018 | Stein et al. | |
| 10,271,965 B2 * | 4/2019 | Dungy | A61F 2/4657 |
| 2002/0029784 A1 | 3/2002 | Stark | |
| 2002/0049394 A1 | 4/2002 | Roy et al. | |
| 2002/0087075 A1 | 7/2002 | Bucholz | |
| 2003/0004518 A1 | 1/2003 | Perren et al. | |
| 2003/0036713 A1 | 2/2003 | Bouton et al. | |
| 2003/0036764 A1 | 2/2003 | Hamada | |
| 2003/0069644 A1 | 4/2003 | Kovacevic et al. | |
| 2003/0114898 A1 | 6/2003 | Von Arx et al. | |
| 2003/0187351 A1 | 10/2003 | Franck et al. | |
| 2003/0187452 A1 | 10/2003 | Smith et al. | |
| 2004/0011365 A1 | 1/2004 | Govari et al. | |
| 2004/0019382 A1 | 1/2004 | Amirouche et al. | |
| 2004/0064073 A1 | 4/2004 | Heldreth | |
| 2004/0105086 A1 | 6/2004 | Leitner et al. | |
| 2004/0131013 A1 | 7/2004 | Ise et al. | |
| 2004/0152970 A1 | 8/2004 | Hunter et al. | |
| 2004/0184351 A1 | 9/2004 | Nishimori et al. | |
| 2004/0215079 A1 | 10/2004 | Omura et al. | |
| 2005/0010299 A1 | 1/2005 | Disilvestro | |
| 2005/0010302 A1 | 1/2005 | Dietz et al. | |
| 2005/0020941 A1 | 1/2005 | Tarabichi | |
| 2005/0033383 A1 | 2/2005 | Ibrahim et al. | |
| 2005/0234555 A1 | 11/2005 | Sutton | |
| 2005/0252294 A1 | 11/2005 | Ariav | |
| 2005/0267485 A1 | 12/2005 | Cordes et al. | |
| 2005/0273170 A1 | 12/2005 | Navarro et al. | |
| 2006/0058798 A1 | 3/2006 | Roman et al. | |
| 2006/0069436 A1 | 3/2006 | Sutton et al. | |
| 2006/0132120 A1 | 6/2006 | Luber et al. | |
| 2006/0161051 A1 | 7/2006 | Terrill-Grisoni et al. | |
| 2006/0173295 A1 | 8/2006 | Zeijlemaker | |
| 2006/0184067 A1 | 8/2006 | Clark et al. | |
| 2006/0195042 A1 | 8/2006 | Flaherty | |
| 2006/0206014 A1 | 9/2006 | Ariav | |
| 2006/0232408 A1 | 10/2006 | Nycz | |
| 2006/0241422 A1 | 10/2006 | Muratayev et al. | |
| 2006/0241569 A1 | 10/2006 | DiSilvestro | |
| 2006/0265026 A1 | 11/2006 | Madjar et al. | |
| 2006/0271112 A1 | 11/2006 | Martinson | |
| 2007/0005145 A1 | 1/2007 | Banks et al. | |
| 2007/0276294 A1 | 1/2007 | Gupta et al. | |
| 2007/0089518 A1 | 4/2007 | Erickson et al. | |
| 2007/0129776 A1 | 6/2007 | Robins et al. | |
| 2007/0173946 A1 | 7/2007 | Bonutti | |
| 2007/0219561 A1 | 9/2007 | Lavallee et al. | |
| 2007/0233065 A1 | 10/2007 | Donofrio et al. | |
| 2007/0233267 A1 | 10/2007 | Amirouche et al. | |
| 2007/0234819 A1 | 10/2007 | Amirouche et al. | |
| 2007/0239165 A1 | 10/2007 | Amirouche | |
| 2007/0239282 A1 | 10/2007 | Caylor, III et al. | |
| 2007/0242652 A1 | 10/2007 | Dahlman et al. | |
| 2007/0255088 A1 | 11/2007 | Jacomson | |
| 2007/0258674 A1 | 11/2007 | Wang | |
| 2007/0272747 A1 | 11/2007 | Woods et al. | |
| 2007/0282451 A1 | 12/2007 | Metzger et al. | |
| 2008/0051908 A1 | 2/2008 | Laurent Anglibaud et al. | |
| 2008/0243266 A1 | 3/2008 | Haynes et al. | |
| 2008/0082118 A1 | 4/2008 | Edidin et al. | |
| 2008/0129486 A1 | 6/2008 | Jeckelmann et al. | |
| 2008/0133016 A1 | 6/2008 | Heinz | |
| 2008/0191584 A1 | 8/2008 | Malkin | |
| 2008/0228195 A1 | 9/2008 | Von Jako et al. | |
| 2008/0228231 A1 | 9/2008 | Raphael et al. | |
| 2009/0005708 A1 | 1/2009 | Johanson | |
| 2009/0069803 A1 | 3/2009 | Starkebaum | |
| 2009/0167719 A1 | 7/2009 | Woolley | |
| 2009/0264894 A1 | 10/2009 | Wasielewski | |
| 2009/0299483 A1 | 12/2009 | Amirouche et al. | |
| 2010/0010494 A1 | 1/2010 | Quirno | |
| 2010/0022874 A1 | 1/2010 | Wang et al. | |
| 2010/0076505 A1 | 3/2010 | Borja | |
| 2010/0076563 A1 | 3/2010 | Otto et al. | |
| 2010/0100010 A1 | 4/2010 | Andarawis | |
| 2010/0100130 A1 | 4/2010 | Carl et al. | |
| 2010/0204575 A1 | 4/2010 | Roche | |
| 2010/0204955 A1 | 4/2010 | Roche | |
| 2010/0151946 A1 | 6/2010 | Wilson et al. | |
| 2010/0191153 A1 | 7/2010 | Sanders et al. | |
| 2010/0198067 A1 | 8/2010 | Mahfouz et al. | |
| 2010/0249665 A1 | 9/2010 | Roche | |
| 2010/0249787 A1 | 9/2010 | Roche | |
| 2010/0249788 A1 | 9/2010 | Roche | |
| 2010/0249790 A1 | 9/2010 | Roche | |
| 2010/0249791 A1 | 9/2010 | Roche | |
| 2010/0320973 A1 | 12/2010 | Nishida | |
| 2010/0328098 A1 | 12/2010 | Stein et al. | |
| 2010/0331633 A1 | 12/2010 | Stein | |
| 2010/0331680 A1 | 12/2010 | Stein | |
| 2010/0331682 A1 | 12/2010 | Stein et al. | |
| 2010/0331734 A1 | 12/2010 | Stein | |
| 2010/0331735 A1 | 12/2010 | Stein | |
| 2010/0331736 A1 | 12/2010 | Stein | |
| 2010/0331737 A1 | 12/2010 | Stein et al. | |
| 2010/0331738 A1 | 12/2010 | Stein et al. | |
| 2011/0004076 A1 | 1/2011 | Janna | |
| 2011/0029913 A1 | 2/2011 | Boillot | |
| 2011/0032184 A1 | 2/2011 | Roche | |
| 2011/0060220 A1 | 3/2011 | Roche | |
| 2011/0092972 A1 | 4/2011 | Allen | |
| 2011/0102455 A1 | 5/2011 | Temple | |
| 2011/0107850 A1 | 5/2011 | Kim et al. | |
| 2011/0160572 A1 | 6/2011 | McIntosh et al. | |
| 2011/0160616 A1 | 6/2011 | Stein et al. | |
| 2011/0160738 A1 | 6/2011 | McIntosh et al. | |
| 2011/0257491 A1 | 10/2011 | Robertson et al. | |
| 2011/0275957 A1 | 11/2011 | Bhandari | |
| 2012/0016362 A1 | 1/2012 | Heinrich et al. | |
| 2012/0022667 A1 | 1/2012 | Accinni et al. | |
| 2012/0035868 A1 | 2/2012 | Roche | |
| 2012/0209117 A1 | 3/2012 | Roche | |
| 2012/0147887 A1 | 6/2012 | Fanson | |
| 2012/0330367 A1 | 12/2012 | Roche et al. | |
| 2013/0023794 A1 | 1/2013 | Stein et al. | |
| 2013/0023795 A1 | 1/2013 | Stein et al. | |
| 2013/0079668 A1 | 3/2013 | Stein et al. | |
| 2013/0079670 A1 | 3/2013 | Stein et al. | |
| 2013/0079671 A1 | 3/2013 | Stein et al. | |
| 2013/0079675 A1 | 3/2013 | Stein et al. | |
| 2013/0079884 A1 | 3/2013 | Stein et al. | |
| 2013/0225982 A1 | 3/2013 | Roche | |
| 2013/0226036 A1 | 8/2013 | Stein et al. | |
| 2013/0261505 A1 * | 10/2013 | Sherman | A61F 2/4657 600/595 |
| 2014/0094715 A1 | 4/2014 | Stein et al. | |
| 2014/0134586 A1 | 5/2014 | Stein et al. | |
| 2014/0135624 A1 | 5/2014 | Stein et al. | |
| 2014/0135655 A1 | 5/2014 | Stein et al. | |
| 2014/0135773 A1 | 5/2014 | Stein et al. | |
| 2014/0276886 A1 | 9/2014 | Stein et al. | |
| 2016/0157940 A1 | 6/2016 | Stein et al. | |

\* cited by examiner

NON-SYMMETRICAL INSERT SENSING SYSTEM AND METHOD THEREFOR

CROSS-REFERENCE TO RELATED APPLICATIONS

Field

The present invention pertains generally to measurement of physical parameters, and particularly to, but not exclusively, medical electronic devices for high precision sensing.

Background

The skeletal system of a mammal is subject to variations among species. Further changes can occur due to environmental factors, degradation through use, and aging. An orthopedic joint of the skeletal system typically comprises two or more bones that move in relation to one another. Movement is enabled by muscle tissue and tendons attached to the skeletal system of the joint. Ligaments hold and stabilize the one or more joint bones positionally. Cartilage is a wear surface that prevents bone-to-bone contact, distributes load, and lowers friction.

There has been substantial growth in the repair of the human skeletal system. In general, orthopedic joints have evolved using information from simulations, mechanical prototypes, and patient data that is collected and used to initiate improved designs. Similarly, the tools being used for orthopedic surgery have been refined over the years but have not changed substantially. Thus, the basic procedure for replacement of an orthopedic joint has been standardized to meet the general needs of a wide distribution of the population. Although the tools, procedure, and artificial joint meet a general need, each replacement procedure is subject to significant variation from patient to patient. The correction of these individual variations relies on the skill of the surgeon to adapt and fit the replacement joint using the available tools to the specific circumstance.

BRIEF DESCRIPTION OF THE DRAWINGS

Various features of the system are set forth with particularity in the appended claims. The embodiments herein, can be understood by reference to the following description, taken in conjunction with the accompanying drawings, in which:

DETAILED DESCRIPTION

Figure 1:
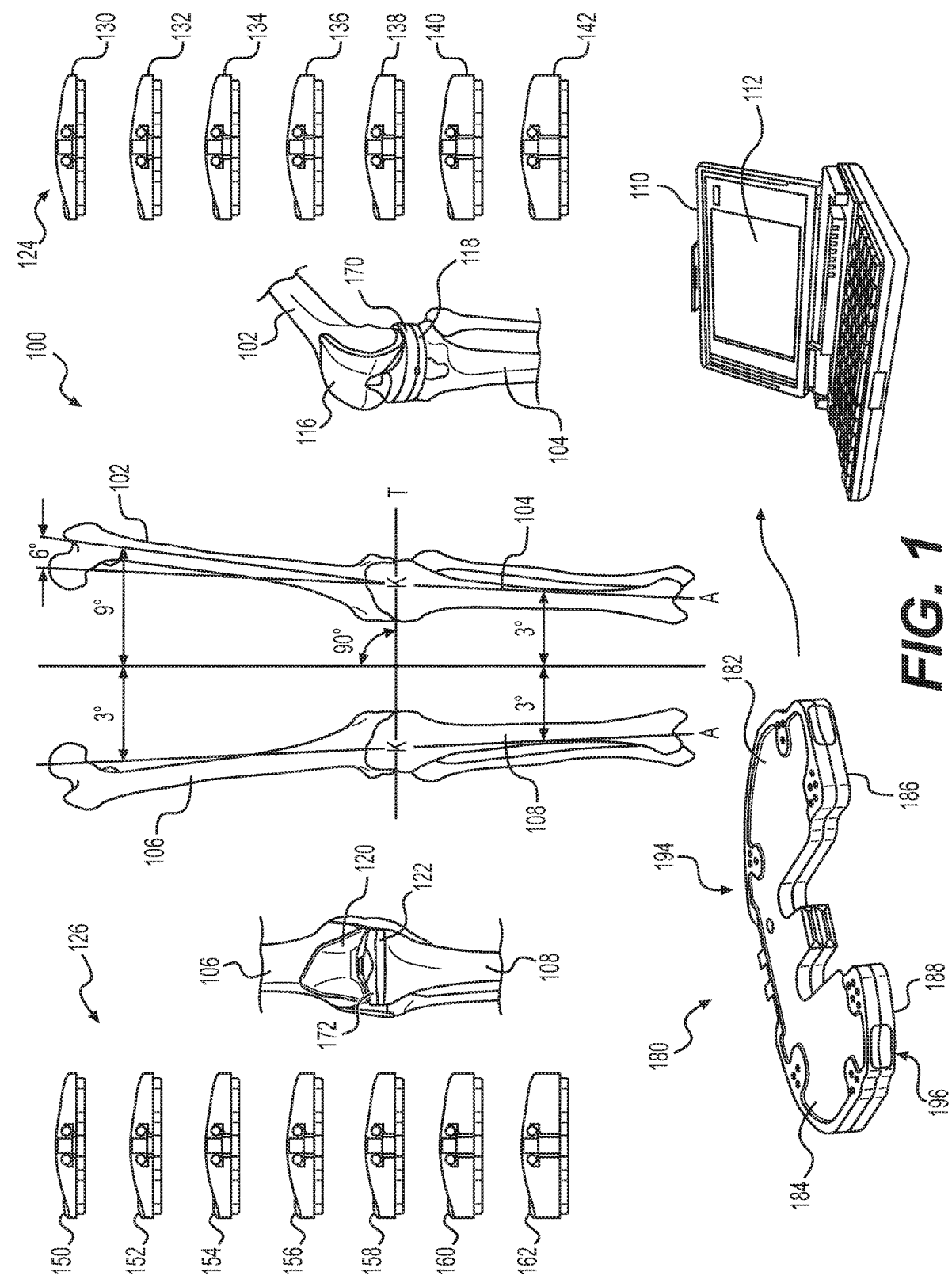
FIG. 1 illustrates an orthopedic measurement system placed in a joint of the musculoskeletal system in accordance with an example embodiment.

Embodiments of the invention are broadly directed to measurement of physical parameters, and more particularly, to fast-response circuitry that supports accurate measurement of small sensor changes.

The following description of embodiment(s) is merely illustrative in nature and is in no way intended to limit the invention, its application, or uses.

For simplicity and clarity of the illustration(s), elements in the figures are not necessarily to scale, are only schematic, are non-limiting, and the same reference numbers in different figures denote the same elements, unless stated otherwise. Additionally, descriptions and details of well-known steps and elements are omitted for simplicity of the description. Notice that once an item is defined in one figure, it may not be discussed or further defined in the following figures.

The terms "first", "second", "third" and the like in the Claims or/and in the Detailed Description are used for distinguishing between similar elements and not necessarily for describing a sequence, either temporally, spatially, in ranking or in any other manner. It is to be understood that the terms so used are interchangeable under appropriate circumstances and that the embodiments described herein are capable of operation in other sequences than described or illustrated herein.

Processes, techniques, apparatus, and materials as known by one of ordinary skill in the art may not be discussed in detail but are intended to be part of the enabling description where appropriate.

The orientation of the x, y, and z-axes of rectangular Cartesian coordinates is assumed to be such that the x and y axes define a plane at a given location, and the z-axis is normal to the x-y plane. The axes of rotations about the Cartesian axes of the device are defined as yaw, pitch and roll. With the orientation of the Cartesian coordinates defined in this paragraph, the yaw axis of rotation is the z-axis through body of the device. Pitch changes the orientation of a longitudinal axis of the device. Roll is rotation about the longitudinal axis of the device.

The orientation of the X, Y, Z axes of rectangular Cartesian coordinates is selected to facilitate graphical display on computer screens having the orientation that the user will be able to relate to most easily. Therefore the image of the device moves upward on the computer display whenever the device itself moves upward for example away from the surface of the earth. The same applies to movements to the left or right.

Although inertial sensors are provided as enabling examples in the description of embodiments, any tracking device (e.g., a GPS chip, acoustical ranging, accelerometer, magnetometer, gyroscope, inclinometers, MEMs devices) can be used within the scope of the embodiments described.

At least one embodiment is directed to a kinetic orthopedic measurement system to aid a surgeon in determining real time alignment, range of motion, loading, impingement, and contact point of orthopedic implants under load. Although the system is generic and can be adapted for use as a measurement device it can used as part in a trialing implant, a permanent implant, or a tool. The measurement device and can be used in the spine, shoulder, knee, hip, ankle, wrist, finger, toe, bone, or musculoskeletal, etc.). In a non-limiting example disclosed herein the measurement device and system is illustrated to support the implantation of a knee joint.

The non-limiting embodiment described herein is related to quantitative measurement based orthopedic surgery and referred to herein as the kinetic system. The kinetic system includes a sensor system that provides quantitative measurement data and feedback that can be provided visually, audibly, or haptically to a surgeon or surgical team. The kinetic system provides the surgeon real-time dynamic data regarding force, pressure, or loading within the musculoskeletal system, contact and congruency through a full range of motion, and information regarding impingement.

In general, kinetics is the study of the effect of forces upon the motion of a body or system of bodies. Disclosed herein is a system for kinetic assessment of the musculoskeletal system. The kinetic system can be for general measurement of the musculoskeletal system, trial installation and measurement of prosthetic components, or long-term monitoring of an installed permanent prosthetic component to the musculoskeletal system. For example, in an installation of a trialing prosthetic component one or more bone surfaces have to be prepared to receive a device or prosthetic component. The kinetic system is designed to take quantitative measurements of at least the load, position of load, or alignment with the forces being applied to the joint similar to that of a final joint installation. The kinetic system can support the actual bone cut for optimal contact point(s), balance, load magnitude, and alignment over a range of motion. The one or more measurement components having sensors are designed to allow ligaments, tissue, and bone to be in place while the quantitative measurement data is taken and reported in real-time. This is significant because the bone cuts take into account the kinetic forces where a kinematic assessment and subsequent bone cuts could be substantial changed from an alignment, load, and position of load once the joint is reassembled. Furthermore, the measurement data can be transmitted to a computer in the operating room that can analyze the measurement data and propose a workflow for the surgical team to yield the desired results. Moreover, the kinetic system supports real-time adjustments such as bone cuts, rotation of a prosthetic component, or ligament tensioning with real-time measurements to validate the surgical procedure or the proposed workflow.

A prosthetic joint installation can benefit from quantitative measurement data in conjunction with subjective feedback of the prosthetic joint to the surgeon. The quantitative measurements can be used to determine adjustments to bone, prosthetic components, or tissue prior to final installation. Permanent sensors can also be housed in final prosthetic components to provide periodic data related to the status of the implant. Data collected intra-operatively and long-term can be used to determine parameter ranges for surgical installation and to improve future prosthetic components. The physical parameter or parameters of interest can include, but are not limited to, measurement of alignment, load, force, pressure, position, displacement, density, viscosity, pH, spurious accelerations, color, movement, particulate matter, structural integrity, and localized temperature. Often, several measured parameters are used to make a quantitative assessment. A graphical user interface can support assimilation of measurement data. Parameters can be evaluated relative to orientation, alignment, direction, displacement, or position as well as movement, rotation, or acceleration along an axis or combination of axes by wireless sensing modules or devices positioned on or within a body, instrument, appliance, vehicle, equipment, or other physical system.

At least one embodiment is directed to a system for adjusting or monitoring a contact position of a musculoskeletal joint for stability comprising: a prosthetic component configured to rotate after being coupled to a bone; a sensed prosthesis having an articular surface where the sensed prosthesis is configured to couple to the prosthetic component, where the sensed prosthesis has a plurality of load sensors coupled to the articular surface and a position measurement system configured to measure position, slope, rotation, or trajectory, and a remote system configured to wirelessly receive quantitative measurement data from the sensed prosthesis where the remote system is configured to display the articular surface, where the remote system is configured to display position of applied load to the articular surface, and where the remote system is configured to report impingement as the musculoskeletal joint is moved through a range of motion (ROM).

While the specification concludes with claims defining the features of the invention that are regarded as novel, it is believed that the invention will be better understood from a consideration of the following description in conjunction with the drawing figures, in which like reference numerals are carried forward.

The example embodiments shown herein below of the measurement device are illustrative only and does not limit use for other parts of a body. The measurement device can be a tool, equipment, implant, or prosthesis that measures at least one parameter or supports installation of prosthetic components to the musculoskeletal system. The measurement device can be used on bone, the knee, hip, ankle, spine, shoulder, hand, wrist, foot, fingers, toes, and other areas of the musculoskeletal system. In general, the principles disclosed herein are meant to be adapted for use in all locations of the musculoskeletal system.

FIG. 1 illustrates an orthopedic measurement system 100 placed in a joint of the musculoskeletal system in accordance with an example embodiment. In the example, orthopedic measurement system 100 is a prosthetic component but can be a tool or device that couples to the musculoskeletal system to provide quantitative measurement data. The prosthetic component can be a temporary installation within a prosthetic joint or a permanent installation. Quantitative measurement data from the prosthetic component is transmitted to a computer 110 having a display 112. Computer 110 can be in proximity to the prosthetic component to provide feedback and analysis of the quantitative measurement data in real-time and displayed on display 112. As shown, orthopedic measurement system 100 is used in an operating room as a trialing device that supports installation of a final prosthetic joint. The trialing device provides quantitative measurement data related to loading, balance, alignment, and motion of the joint. In one embodiment, the prosthetic component includes a plurality of sensors to generate quantitative measurement data. The prosthetic component is made similar to the final prosthetic component such that the quantitative measurement data transfers or will be equivalent to what the final prosthetic component will see. A final prosthetic component can also have a plurality of sensors for providing quantitative measurement data long-term. As shown, the orthopedic measurement system 100 is used for a prosthetic knee joint installation but can be adapted for a hip joint, ankle joint, shoulder joint, elbow, spine, knee hand, foot, wrist, other joints, non-joint applications related to the musculoskeletal system, bone, or orthopedic measurements.

In general, orthopedic measurement system 100 is coupled to or in proximity to the musculoskeletal system to measure a parameter. In a non-limiting example, orthopedic measurement system 100 is used to measure parameters that support a procedure such as an installation of an artificial joint. Embodiments of orthopedic measurement system 100 are broadly directed to measurement of physical parameters such as load, position of load, temperature, pH, alignment, position, wear, prosthesis bond strength, color, infection, or turbidity to name but a few. In-situ measurements such as load magnitude and position of load during orthopedic joint implant surgery would be of substantial benefit to verify an implant is in balance and under appropriate loading or tension. In one embodiment, the instrument is similar to and operates with other instruments currently used by surgeons. Thus, the surgeon needs minimal training on the use of the prosthetic component with sensors such that orthopedic measurement system 100 can be incorporated into the procedure with little or no increase in surgical time, yet yield quantitative measurement data that can be used to verify subjective field as well as indicate if an issue is present. Moreover, this stimulates acceptance of the technology thereby reducing the adoption cycle of orthopedic measurement system 100. The surgeon can install prosthetic components within predetermined ranges determined by quantitative measurement data that maximizes the working life of the joint prosthesis and reduce costly revisions based on clinical evidence.

Orthopedic measurement system 100 generates quantitative measurement data specific for a patient installation that is also part of a larger database that is used for assessment and long-term analysis and trends on prosthetic joint operation and reliability. For example, orthopedic measurement system 100 can be used as a trialing device to generate data in real-time to support measurement of the musculoskeletal system. Alternatively, orthopedic measurement system 100 can be used as a permanent device to monitor the patient musculoskeletal system over an extended period of time. In the example, orthopedic measurement system 100 comprises a prosthetic component having one or more sensors configured to provide quantitative measurement data when installed in the musculoskeletal system. The quantitative measurement data is used to support optimal installation of a prosthetic joint or prosthetic component. A transceiver in orthopedic measurement system 100 can transmit the measurement data to a computer 110. Computer 110 has a display 112 whereby the measurement results can be shown and updated as changes are made in real-time to support installation using the quantitative measurement data. In one embodiment, computer 110 and display 112 are placed in an operating room where the quantitative measurement data is provided to a surgeon for immediate review. Computer 110 can be programmed to convert the measurement data into a visual, audible, or haptic format that supports providing the information in a manner that the surgeon can use in real-time and plan a next step based on quantitative measurement data.

A left leg comprises a femur 102 and a tibia 104. In the example, the orthopedic system 100 supports a total or partial knee arthroplasty for a left knee or a right knee. A left total knee arthroplasty comprises a femoral prosthetic component 116 of a first type, an insert 170 of a first type, and a tibial prosthetic component 118 of a first type. In general, the prosthetic components of the first type are specific to the left leg, are non-symmetric, and are not suitable to be used on a right leg. Bone cuts are required to prepare surfaces for receiving the prosthetic components. The bone cuts can also support alignment of femur 102 and tibia 104 to a mechanical axis of the leg. Femoral prosthetic component 116 couples to a distal end of femur 102. Tibial prosthetic component 118 couples to a proximal end of tibia 104. An insert 170 couples to and is retained by the tibial prosthetic component 118. Typically, insert 170 is placed in a tibial tray of tibial prosthetic component 118. Insert 170 has at least one articular surface that couples to a corresponding condyle of femoral prosthetic component 116 to support movement of the prosthetic left knee joint. The left prosthetic knee joint is retained by the ligaments and tendons of the left knee.

Insert 170 for the left prosthetic knee joint comprises a shim and a measurement module 180. The shim couples to measurement module 180 to form insert 170. A plurality of shims 124 of the first type are provided to adjust the height of insert 170. Each shim of plurality of shims 124 corresponds to an insert height of a final insert or permanent insert of the first type that will be installed into the final knee joint after the correct shim height, insert rotation, range of motion, alignment, load magnitude, or position of load is identified through quantitative measurement. In general, after installation of femoral prosthetic component 116 and tibial prosthetic component 118 a shim from plurality of shims 124 is selected. The shim selected is chosen to produce a height on insert 170 that when inserted in the prosthetic knee joint will place the ligaments and tendons under tension such that the knee joint optimally loads insert 170. If insert 170 is too tight within the prosthetic knee joint (e.g. measured pressure is too high) then the shim is removed and a shim of lesser height from the plurality of shims 124 is placed with measurement module 180. Re-inserting insert 170, with the lesser height shim should produce a lower pressure reading on the articular surfaces. The process of shim replacement and reinserting insert 170 in the prosthetic knee joint can continue until an optimal pressure is found. In general, the surgeon makes the bone cuts for a predetermined insert height 170. In one embodiment, a pressure range can be compared to the measured pressure applied to insert 170. For example, a red light— green light could be used on display 112 to notify the surgeon that the pressure is within an acceptable range or out of range thereby requiring a change of shim. The left prosthetic knee joint could be difficult to move through a range of motion under high loading. If insert 170 measures a low pressure within the prosthetic knee joint (e.g. too loose) the shim is removed and a shim from the plurality of shims 124 having an increased height replaces the previous shim. Re-inserting insert 170 in the prosthetic knee with different shims can continue until an optimal pressure is found.

In the example, plurality of shims 124 comprises 7 shims each having a different height. In one embodiment, plurality of shims 124 comprises shims 130, 132, 134, 136, 138, 140, and 142 respectively having a height with module 180 attached of 10, 11, 12, 13, 14, 16, and 18 millimeters. There will also be a corresponding set of final inserts of 10, 11, 12, 13, 14, 16, and 18 millimeters that will replace insert 170 in the joint when an optimal insert height has been selected. As mentioned previously, plurality of shims 124 are of a first type that can be used for a left prosthetic knee joint. Each shim of plurality of shims 124 is non-symmetrical. In one embodiment, each shim of plurality of shims 124 is non-symmetrical about an anterior-posterior axis. Each shim of the plurality of shims 124 has a medial articular surface and a lateral articular surface to support movement of the left prosthetic knee joint. In one embodiment, the medial articular surface differs from the lateral articular surface in area, contour, or shape on each shim of plurality of shims 124.

Measurement module 180 includes one or more sensors to measure one or more parameters of the musculoskeletal system. Parameters that can be measured by measurement module 180 can include force, pressure, load, position of load, tension, shear, relative position, acceleration, velocity, absolute position, temperature, pH, bone density, fluid viscosity, temperature, strain, angular deformity, vibration, venous flow, lymphatic flow, load, torque, distance, tilt, rotation, shape, elasticity, motion, bearing wear, subsidence, bone integration, change in viscosity, turbidity, kinematics, stability, or vascular flow. Measurement module 180 further includes a tracking system that can measure position, rotation, and slope. In one embodiment, the tracking system comprises inertial sensors, accelerometers, a GPS chip, acoustical ranging, magnetometers, gyroscopes, inclinometers, or MEMs sensors that measure up to 9 degrees of freedom. Data collected intra-operatively and long term can be used to determine parameter ranges for surgical installation and to improve future prosthetic components. Parameters can be evaluated relative to orientation, alignment, direction, displacement, or position as well as movement, rotation, or acceleration along an axis or combination of axes by wireless sensing modules or devices positioned on or within a body, instrument, appliance, vehicle, equipment, or other physical system.

Measurement module 180 couples to a selected shim of plurality of shims 124 to form insert 170. Measurement module 180 has a first side 194 and a second side 196. The first side 194 of measurement module 180 comprises a medial surface 182 and a lateral surface 184. The medial surface 182 of measurement module 180 differs in area, contour, or shape from the lateral surface 184 of measurement module 180. In one embodiment, medial surface 182 and lateral surface 184 is non-symmetrical about the anterior-posterior axis. The medial surface 182 and the lateral surface 184 respectively couples to the medial articular surface and the lateral articular surface of the selected shim of plurality of shims 124. In one embodiment, measurement module 180 includes a first plurality of load sensors underlying medial surface 182 and a second plurality of load sensors underlying lateral surface 184 of measurement module 180. Loading applied to the medial articular surface and the lateral articular surface of the selected shim of the first type respectively loads medial surface 182 and lateral surface 184 of measurement module 180. Electronic circuitry in measurement module 180 couples to the first and second plurality of load sensors. The electronic circuitry is configured to support a measurement process and transmit measurement data. In one embodiment, the first plurality of load sensors couples between the medial surface 182 on the first side 194 of measurement module 180 and the medial surface 186 on the second side 196 of measurement module 180. Similarly, the second plurality of load sensors couples between the lateral surface 184 on the first side 194 of measurement module 180 and the lateral surface 188 on the second side 196 of the measurement module 180. In the example, measurement module 180 is configured to receive a compressive loading by the musculoskeletal system.

Orthopedic measurement system 100 further supports installation of a right prosthetic knee joint. A right leg comprises a femur 106 and a tibia 108. In the example, the orthopedic system 100 can support a total right knee arthroplasty or a partial knee joint repair. A right total knee arthroplasty comprises a femoral prosthetic component 120 of a second type, an insert 172 of a second type, and a tibial prosthetic component 122 of a second type. In general, the prosthetic components of the second type are specific to the right leg and are not suitable to be used on a left leg. Bone cuts are required to prepare surfaces for receiving the prosthetic components. The bone cuts can also support alignment of femur 106 and tibia 108 to a mechanical axis of the leg. Femoral prosthetic component 120 couples to a distal end of femur 106. Tibial prosthetic component 122 couples to a proximal end of tibia 108. Insert 172 couples to and is retained by tibial prosthetic component 122. Typically, insert 172 is placed in a tibial tray of tibial prosthetic component 122. Insert 172 has at least one articular surface that couples to a corresponding condyle of femoral prosthetic component 120 to support movement of the prosthetic right knee joint. The right prosthetic knee joint is retained by the ligaments and tendons of the right knee thereby applying a compressive force on insert 172.

Insert 172 for the right prosthetic knee joint comprises a selected shim of plurality of shims 126 of the second type and measurement module 180. The selected shim of the second type couples to measurement module 180 to form insert 170. In one embodiment, second side 196 of measurement module 180 couples to the selected shim of plurality of shims 126. The second side 196 of measurement module 180 has a medial surface 186 and a lateral surface 188 that respectively couples to the medial articular surface and the lateral articular surface of the selected shim of plurality of shims 126 of the second type. In one embodiment, the second side 196 of measurement module 180 is non-symmetrical about the anterior-posterior axis. The medial surface 186 differs from lateral surface 188 in area, contour, or shape. Thus, the first side 194 of measurement module couples to the selected shim of the first type of the plurality of shims 124 and the second side 196 of measurement module 180 couples to the selected shim of the second type of the plurality of shims 126. The plurality of shims 126 of the second type are provided to adjust the height of insert 172. Each shim of plurality of shims 126 corresponds to an insert height of a final insert or permanent insert of the second type that will be installed after the correct shim height, insert rotation, range of motion, alignment, load magnitude, or position of load is identified through quantitative measurement. In general, after installation of femoral prosthetic component 120 and tibial prosthetic component 122 a shim from plurality of shims 126 is selected. The selected shim is chosen to produce a height on insert 172 that when inserted in the right prosthetic knee joint will result in the ligaments and tendons of the knee joint optimally loading insert 172 of the second type. If insert 172 is too tight within the prosthetic knee joint (e.g. measured pressure is too high) then the shim is removed and a shim from the plurality of shims 126 having a lesser height replaces the previous shim. Re-inserting insert 170 with the shim of lesser height should produce a lower pressure reading and also support freer movement of the right knee joint. The process of shim replacement and reinserting insert 172 in the prosthetic right knee joint can continue until an optimal pressure is found. In one embodiment, a known optimal pressure range can be compared to the measured pressure applied to insert 172. For example, a red light—green light could be used on display 112 to notify the surgeon that the pressure is within an acceptable range or out of range thereby requiring a change of shim. Orthopedic measurement system 100 can further produce a workflow to select a shim or make an adjustment based on the measurement data. If insert 172 measures a low pressure within the prosthetic knee joint (e.g. too loose) the selected shim is removed and a shim from the plurality of shims 126 having an increased height replaces the previously selected shim. Re-inserting insert 172 in the prosthetic knee with different shims of increased height can continue until an optimal pressure is found.

In the example, plurality of shims 126 comprises 7 shims each having a different height. In one embodiment, plurality of shims 126 comprises shims 150, 152, 154, 156, 158, 160, and 162 respectively having a height with module 180 attached of 10, 11, 12, 13, 14, 16, and 18 millimeters. There will also be a corresponding set of final inserts or permanent inserts of 10, 11, 12, 13, 14, 16, and 18 millimeters that will replace insert 172 in the right knee joint when an optimal insert height has been selected. The measurements from shims 126 and module 180 should correspond to what is seen on the final inserts. As mentioned previously, plurality of shims 126 are of the second type that can be used for a prosthetic right knee joint. Each shim of plurality of shims 126 is non-symmetrical. In one embodiment, each shim of plurality of shims 126 is non-symmetrical about an anterior-posterior axis. Each shim of the plurality of shims 126 has a medial articular surface and a lateral articular surface to support movement of the prosthetic right knee joint. In one embodiment, the medial articular surface differs from the lateral articular surface in area, contour, or shape on each shim of plurality of shims 126.

In general, orthopedic measurement system comprises plurality of shims 124 of the first type, plurality of shims 126 of the second type, measurement module 180, and a computer 110. Shims of the first type are configured for use in a prosthetic left knee joint and cannot be used in a prosthetic right knee joint. Similarly, shims of the second type are configured for use in a prosthetic right knee joint and cannot be used in a prosthetic left knee joint. Plurality of shims 126 each have a medial articular surface and a lateral articular surface that are non-symmetrical about the anterior-posterior axis. Plurality of shims 126 each have a medial articular surface and a lateral articular surface that are non-symmetrical about the anterior posterior axis. In one embodiment, the medial articular surface of each shim of plurality of shims 126 differs from the lateral articular surface by area, contour, or shape. Measurement module 180 has medial surface 182 and lateral surface 184 on first side 194. Similarly, measurement module 180 has medial surface 186 and lateral surface 188 on second side 196. In one embodiment measurement module 180 is configured to measure loading applied to one of the plurality of shims 124 or one of the plurality of shims 126 when installed respectively in a prosthetic left knee joint or a prosthetic right knee joint. First side 194 of measurement module 180 is configured to couple to one of plurality of shims 124 when forming insert 170. Second side 196 is configured to couple to one of plurality of shims 126 to when forming when forming insert 172. The use of a single measurement module 180 for non-symmetrical right and left total knee arthroplasty reduces cost and the number of components required. In one embodiment, the plurality of shims 124 and shims 126 comprise a molded polymer. For example, polymers such as polyurethane, PEEK, or polycarbonate can be used in an injection molding process to form plurality of shims 124 and shims 126. Similarly, the housing of measurement module 180 can be an injection molded polymer. The use of non-symmetrical shims for prosthetic right and left knee joints results in an insert that can support the movement and loads of similar to a natural knee joint. Loading, movement, and contact area on the medial and lateral sides of the knee joint are likely not symmetrical. Quantitative measurement data will be used to learn how to distribute the medial-lateral loading and adjust the area, contour, and shape of the medial and lateral articular surfaces of the shim to support more natural movement.

Figure 2:
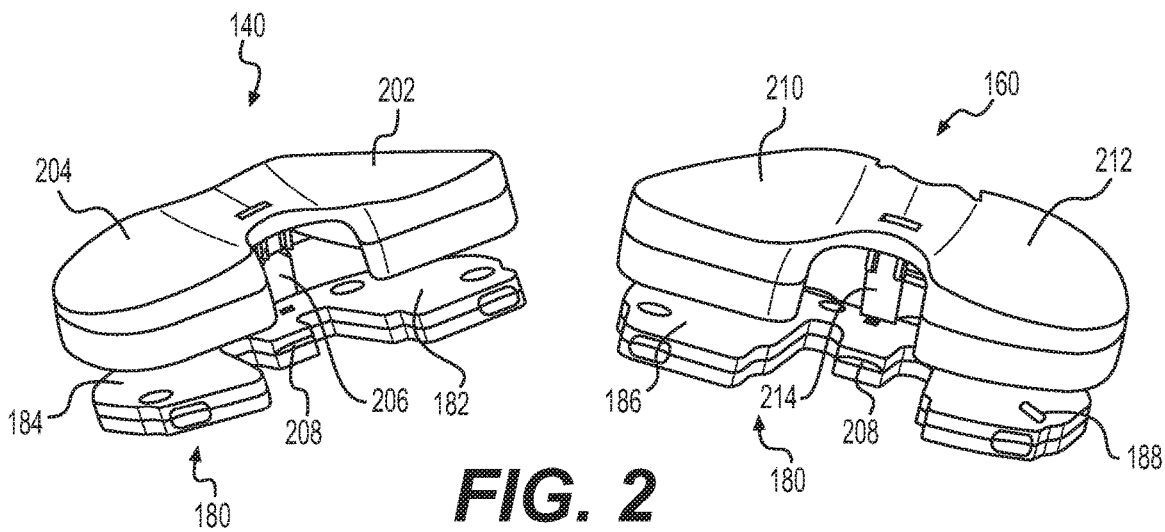
FIG. 2 is an illustration of the measurement module with a first shim of a first type and a second shim of a second type and in accordance with an example embodiment.

FIG. 2 is an illustration of measurement module 180 with shim 140 and shim 160 in accordance with an example embodiment. Shim 140 is of the first type for a prosthetic left knee joint. Shim 160 is of the second type for a prosthetic right knee joint. Shim 140 is a 16 millimeter shim from plurality of shims 124 shown in FIG. 1. Shim 160 is a 16 millimeter shim from plurality of shims 126 shown in FIG. 1. Shim 140 and shim 160 are not interchangeable. In one embodiment, measurement module 180 is configured to couple to shim 140 or shim 160 where shim 140 couples to a first side of measurement module 180 and shim 160 couples to a second side of measurement module 180. In general plurality of shims 124 and plurality of shims 126 have at least one retaining feature configured to retain a shim to measurement module 180. Shim 140 has a retaining feature 206 configured to couple to a retaining feature 208 on a posterior side of measurement module 180. In one embodiment, retaining feature 206 is a flexible tab having a projection extending from a surface of retaining feature 206. The projection of retaining feature 206 is configured to couple within a slot or groove 208 of measurement module 180 when shim 140 couples to measurement module 180. In one embodiment, shim 140 and measurement module 180 also have retaining features on an anterior side. Similarly, shim 160 has a retaining feature 214 configured to couple to retaining feature 208 on the posterior side of measurement module 180. In one embodiment, retaining feature 214 is a flexible tab having a projection extending from a surface of retaining feature 214. The projection of retaining feature 214 is configured to couple within a slot or groove 208 of measurement module 180 when shim 160 couples to measurement module 180. In one embodiment, shim 160 and measurement module 180 also have retaining features on the anterior side. Each of the remaining plurality of shims 124 and the remaining plurality of shims 126 shown in FIG. 1 will respectively couple to measurement module 180 in a similar fashion as shim 140 and shim 160. Retaining feature 208 or retaining feature 214 respectively couple to groove 208 of measurement module 180 under force. Measurement module 180 is removed from shim 140 or shim 160 by respectively bending retaining features 208 or 214 away from groove 208 such that measurement module 180 can be removed.

Shim 140 has a medial articular surface 202 and lateral articular surface 204. Articular medial surface 202 and lateral articular surface 204 of shim 140 supports movement of a prosthetic left knee joint. Shim 140 is shown overlying measurement module 180 to illustrate the orientation to couple shim 140 to measurement module 180. Medial surface 182 and lateral surface 184 of measurement module 180 respectively couples to medial articular surface 202 and lateral articular surface 204 of shim 140. Thus, the first side of measurement module 180 couples to shim 140. In one embodiment, measurement module 180 is non-symmetrical about an anterior-posterior axis. Medial surface 182 differs in area, contour, or shape from lateral surface 184 of measurement module 180. Loading applied to medial articular surface 202 and lateral articular surface 204 by the femoral prosthetic component respectively couples to medial surface 182 and lateral surface 184 of measurement module 180. In one embodiment, measurement module 180 measures load magnitude at three or more locations on medial surface 182 and at three or more locations on lateral surface 184. The measurement data is sent to computer 110 of FIG. 1. Computer 110 of FIG. 1 can calculate a load magnitude and a position of load in real-time on medial surface 182 and lateral surface 184 which corresponds to a load magnitude and position of load on medial articular surface 202 and lateral articular surface 204.

Shim 160 has a medial articular surface 210 and lateral articular surface 212. Articular medial surface 210 and lateral articular surface 212 of shim 160 supports movement of a prosthetic right knee joint. Shim 160 is shown overlying measurement module 180 to illustrate the orientation to couple shim 160 to measurement module 180. Medial surface 186 and lateral surface 188 of measurement module 180 respectively couples to medial articular surface 210 and lateral articular surface 212 of shim 160. Thus, the second side of measurement module 180 couples to shim 160. In one embodiment, measurement module 180 is non-symmetrical about an anterior-posterior axis. Medial surface 186 differs in area, contour, or shape from lateral surface 188 of measurement module 180. Loading applied to medial articular surface 210 and lateral articular surface 212 by the femoral prosthetic component respectively couples to medial surface 186 and lateral surface 188 of measurement module 180. In one embodiment, measurement module 180 measures load magnitude at three or more locations on medial surface 186 and at three or more locations on lateral surface 188. The measurement data is sent to computer 110 of FIG. 1. Computer 110 of FIG. 1 can calculate a load magnitude and a position of load in real-time on medial surface 186 and lateral surface 188 which corresponds to a load magnitude and position of load on medial articular surface 210 and lateral articular surface 212.

Figure 3:
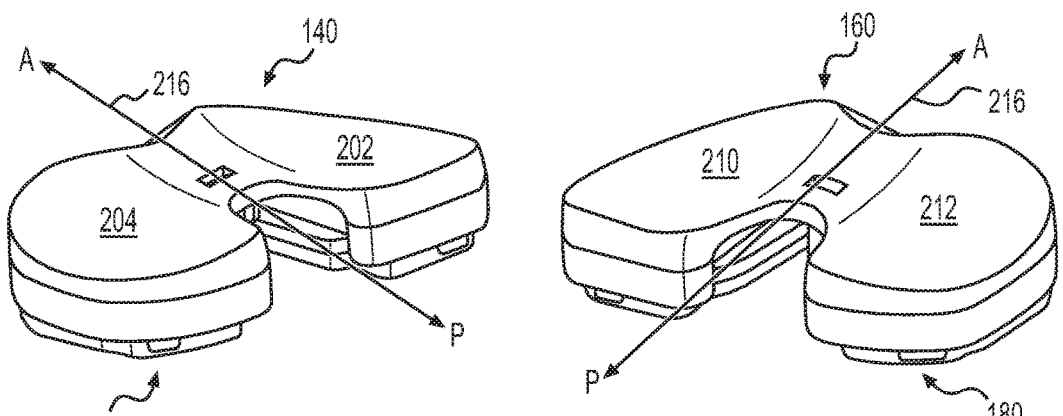
FIG. 3 is a top view of the first shim coupled to the measurement module and the second shim coupled to the measurement module in accordance with an example embodiment.

FIG. 3 is a top view of shim 140 coupled to measurement module 180 and shim 160 coupled to measurement module 180 in accordance with an example embodiment. Shim 140 and measurement module 180 has one or more retaining features that couples shim 140 to measurement module 180. The retaining features allow the shim to be released and removed from measurement module 180. The first side of measurement module 180 having medial surface 182 and lateral surface 184 as shown in FIG. 1 couples to shim 140. Once shim 140 is removed, a different shim of a different height from the plurality of shims 124 can be coupled to measurement module 180. An anterior-posterior axis is represented by double arrow line 216. Medial articular surface 202 is on medial side of double arrow line 216 and lateral articular surface 204 is on the lateral side of double arrow line 216. Shim 140 is non-symmetrical about the anterior-posterior axis. In the example, medial articular surface 202 differs from lateral articular surface 204 by area, contour, or shape.

Measurement module 180 can be removed from shim 140 and coupled to shim 160. Shim 160 and measurement module 180 has one or more retaining features that couples shim 160 to measurement module 180. The retaining features allow the shim to be released and removed from measurement module 180. The second side of measurement module 180 having medial surface 186 and lateral surface 188 as shown in FIG. 1 couples to shim 160. Once shim 160 is removed, a different shim of a different height from the plurality of shims 126 can be coupled to measurement module 180. An anterior-posterior axis is represented by double arrow line 219. Medial articular surface 210 is on a medial side of double arrow line 216 and lateral articular surface 212 is on the lateral side of double arrow line 216. Shim 160 is non-symmetrical about the anterior-posterior axis. In the example, medial articular surface 210 differs from lateral articular surface 212 by area, contour, or shape.

Figure 4:
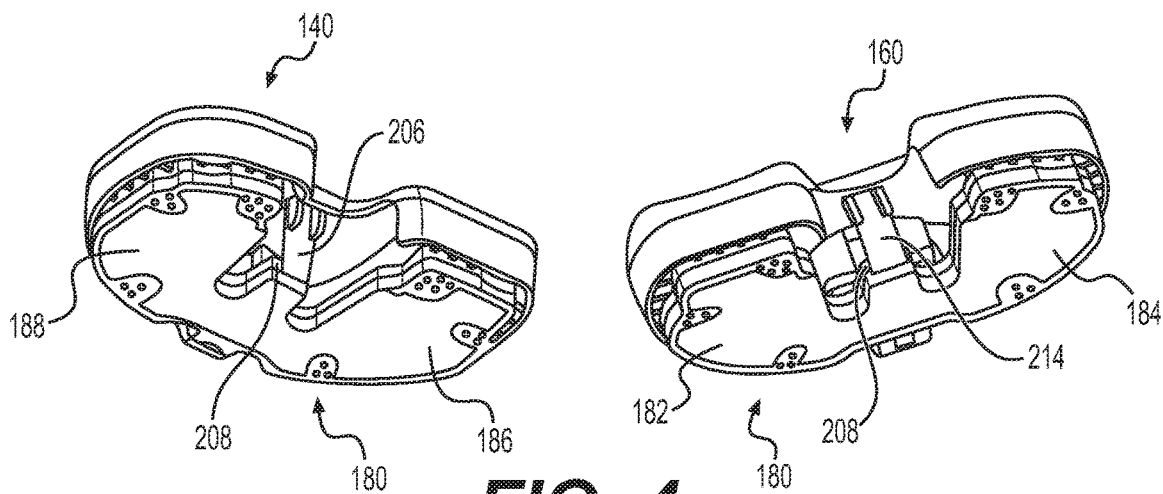
FIG. 4 is a bottom view of the first shim coupled to the measurement module and a bottom view of the second shim coupled to the measurement module in accordance with an example embodiment.

FIG. 4 is a bottom view of shim 140 coupled to measurement module 180 and a bottom view of shim 160 coupled to measurement module 180 in accordance with an example embodiment. Medial surface 186 and lateral surface 188 on the second side of measurement module 180 can be seen from the bottom view when coupled to shim 140. Retaining feature 206 of shim 140 is shown coupling to groove 208 of measurement module 180. In one embodiment, the projection extending from a surface of retaining feature 206 of shim 140 fits in the groove 208 of measurement module 180 when shim 140 couples to measurement module 180. Shim 140 can be removed from measurement module 180 by flexing retaining feature 206 of shim 140 away from groove 208 of measurement module 180. Shim 140 can be separated from measurement module 180 when the projection of retaining feature 206 is outside groove 208.

Shim 140 can be removed from measurement module 180 and shim 160 coupled to measurement module 180. Medial surface 182 and lateral surface 184 on the first side of measurement module 180 can be seen from the bottom view when coupled to shim 160. Retaining feature 214 of shim 160 is shown coupling to groove 208 of measurement module 180. In one embodiment, the projection extending from a surface of retaining feature 214 of shim 160 fits in the groove 208 of measurement module 180 when shim 160 couples to measurement module 180. Shim 160 can be removed from measurement module 180 by flexing retaining feature 214 of shim 160 away from groove 208 of measurement module 180. Shim 160 can be separated from measurement module 180 when the projection of retaining feature 214 is outside groove 208.

Figure 5:
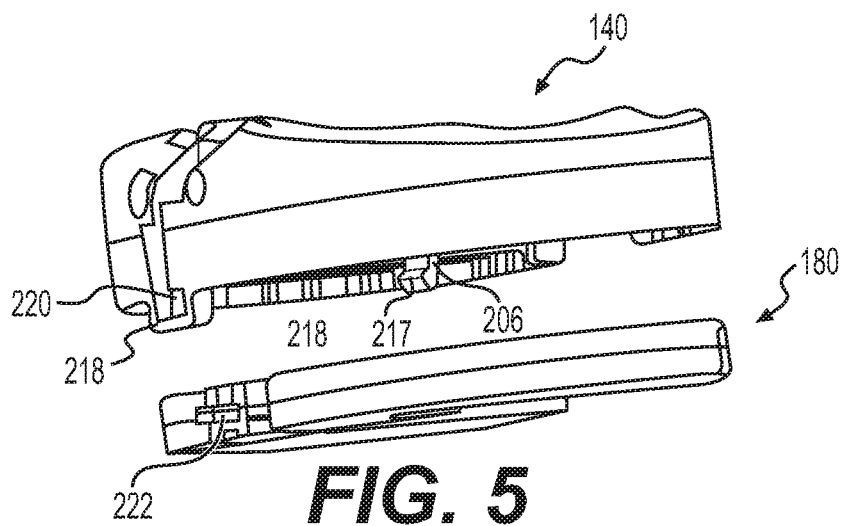
FIG. 5 is an illustration of anterior retaining features for the first shim and the measurement module in accordance with an example embodiment.

FIG. 5 is an illustration of anterior retaining features for shim 140 and measurement module 180 in accordance with an example embodiment. The anterior retaining and the posterior retaining features in the illustration are also on each shim of plurality of shims 124 and each shim of plurality of shims 126 of FIG. 1 and couple together with measurement module 180 similarly as disclosed herein. Insert 170 has a height of 16 millimeters when shim 140 is coupled to measurement module 180. An anterior of shim 140 has a retaining feature 218 that includes a slot 220. An anterior of measurement module 180 has a post 222 configured to fit within slot 220 when coupled together to prevent separation. Also shown is retaining feature 206 of shim 140. Retaining feature 206 includes projection 217 extending from the surface of retaining feature 206. Projection 217 fits in groove 208 of measurement module 180 as shown in FIG. 2.

Figure 6:
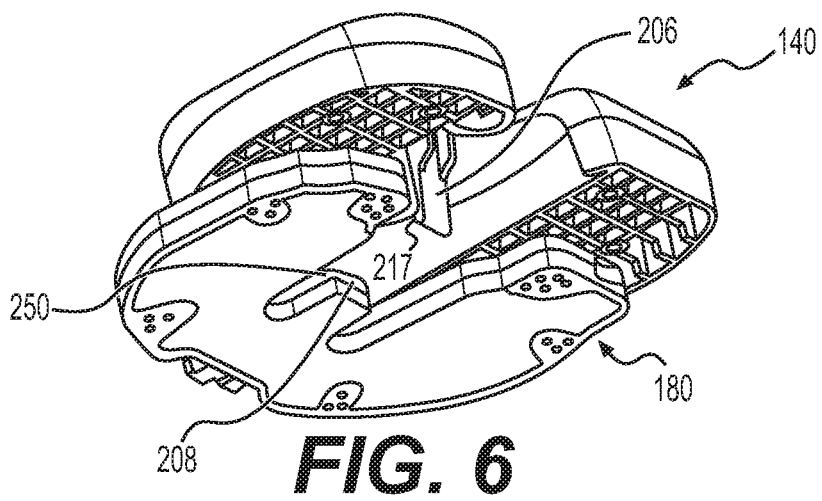
FIG. 6 is an illustration of posterior retaining features for the first shim and the measurement module in accordance with an example embodiment.

FIG. 6 is an illustration of posterior retaining features for shim 140 and measurement module 180 in accordance with an example embodiment. Shim 140 has retaining feature 206 with projection 217 configured to fit in groove 208 of measurement module 180. In one embodiment, post 222 of measurement module 180 is first inserted into opening 220 of retaining feature 218 of shim 140 of FIG. 5 such that the anterior of shim 140 and measurement module 180 are coupled together. The posterior side of shim 140 and measurement module 180 can be coupled together by applying a compressive force to shim 140 and measurement module 180. As mentioned previously retaining feature 206 is flexible. The compressive force applied to shim 140 and measurement module 180 flexes retaining feature past a surface 250 of measurement module 180 and places projection 217 into groove 208 where it retains shim 140 to measurement module 180 to form insert 170. In one embodiment, projection 217 has a contour that supports movement and reduces friction of projection 217 as it moves over surface 250 into groove 208. Shim 140 can be rapidly separated from measurement module 180 by flexing retaining feature 206 away from groove 208 of measurement module 180 and lifting shim 140 away from measurement module 180. Retaining feature 206 has to be flexed enough such that projection 216 clears the surface 250 of measurement module 180.

Figure 7:
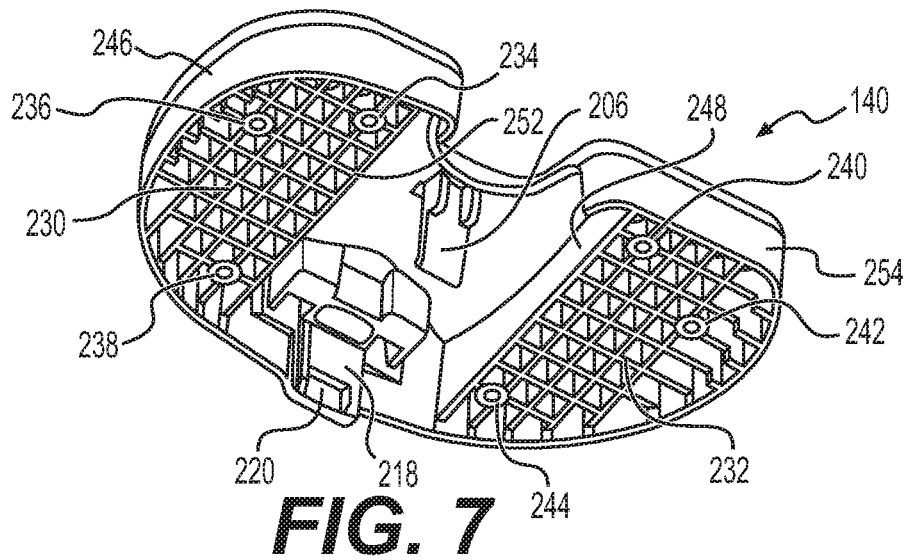
FIG. 7 is a bottom view of the first shim in accordance with an example embodiment.

FIG. 7 is a bottom view of shim 140 in accordance with an example embodiment. The structural elements described herein below will be used on at least one shim of plurality of shims 124 of FIG. 1. Shim 140 is of the first type for the left knee joint. Shim 140 has medial articular surface 202 and lateral articular surface 204 as shown in FIG. 2. Retaining structure 206 of shim 140 is shown in a distal location of shim 140 for coupling to measurement module 180 of FIG. 6. As previously mentioned, retaining structure 206 is flexible. A retaining structure 208 is shown at an anterior location of shim 140. Retaining structure 208 includes an opening 220 configured to receive post 222 of measurement module 180 of FIG. 6. A plurality of columns couple to medial articular surface 202. Similarly, a plurality of columns couple to lateral articular surface 204. The plurality of columns that couple to the medial or lateral articular surface are placed at vertexes of a polygon. Columns 240, 242, and 244 couple to medial articular surface 202 of FIG. 2 defining a first triangle and columns 234, 236, and 238 couple to lateral articular surface 204 of FIG. 2 defining a second triangle. In on embodiment, the first triangle defined by columns 240, 242, and 244 corresponds to a first measurement area on medial articular surface 202 of FIG. 2. In one embodiment, the second triangle defined by columns 234, 236, and 238 corresponds to a second measurement area on lateral articular surface 204 of FIG. 2 In one embodiment, the first triangle or the second triangle has respectively less area than medial articular surface 202 or the lateral articular surface 204 of FIG. 2. In one embodiment, load magnitude and position of load can be measured outside the first and second triangle areas respectively defined by columns 240, 242, and 244 and columns 234, 236, and 238. As mentioned previously, medial articular surface 202 of shim 140 differs in area, contour, or shape from lateral articular surface 204 of shim 140. Similarly, the first triangle defined by columns 240, 242, and 244 can differ by area or shape from the second triangle defined by columns 234, 236, and 238.

In general, the area of the first or second triangles are a subset respectively of medial articular surface 202 and lateral articular surface 204 of FIG. 2. A medial condyle and a lateral condyle of the femoral prosthetic component respectively couples to medial articular surface 202 and lateral articular surface 204 of shim 140 as shown in FIG. 1. In one embodiment, the contact point of the medial or lateral condyle of the femoral prosthetic component respectively couples within the first or second triangle areas over the range of motion. In one embodiment, the left knee joint could be compromised if a contact point is outside the polygon defined by columns within each of the plurality of shims 124.

A structural webbing 232 and 230 is respectively placed within an interior medial cavity and an interior lateral cavity of shim 140. Structural webbing 232 and 230 stiffens shim 140 and reduces flexing of shim 140 under loading by the musculoskeletal system. Structural webbing 232 couples between a sidewall 254 of shim 140 and columns 240, 242, and 244. Structural webbing 232 also couples between columns 240, 242, and 244. In one embodiment, structural webbing 232 couples between an internal wall 248 and columns 240, 242, and 244. Structural webbing 232 can also couple between sidewall 254 and internal wall 248. Structural webbing 232 also prevents the flexing of columns 240, 242, and 244.

Similarly, structural webbing 230 couples between a sidewall 246 of shim 140 and columns 234, 236, and 238. In one embodiment, structural webbing 230 couples between an internal wall 252 and columns 234, 236, and 238. Structural webbing 230 can also couple between sidewall 246 and internal wall 252. Structural webbing prevents flexing of columns 240, 242, and 244 on the lateral side of shim 140. In one embodiment, columns 240, 242, and 244 respectively extend past structural webbing 232 such that columns 240, 242, and 244 couple to medial surface 182 of measurement module 180 of FIG. 1 when shim 140 is coupled to measurement module 180. Thus, structural webbing 232 does not couple to medial surface 182 of measurement module 180 of FIG. 1. In one embodiment, columns 234, 236, and 238 extend past structural webbing 230 such that columns 234, 236, and 238 couple to lateral surface 184 of measurement module 180 of FIG. 1 when shim 140 is coupled to measurement module 180. Structural webbing 230 does not couple to lateral surface 184 when shim 140 is coupled to measurement module 180. In one embodiment, columns 240, 242, and 244 couple loading applied to shim 140 to measurement module 180 on the medial side to underlying force, pressure, or load sensors. In one embodiment, columns 234, 236, and 238 couple loading applied to shim 140 on the lateral side to underlying force, pressure, or load sensors. Although shim 140 is used as an example, the structure of shim 140 as disclosed herein applies to and can be used on each shim of plurality of shims 124 and plurality of shims 126.

Figure 8:
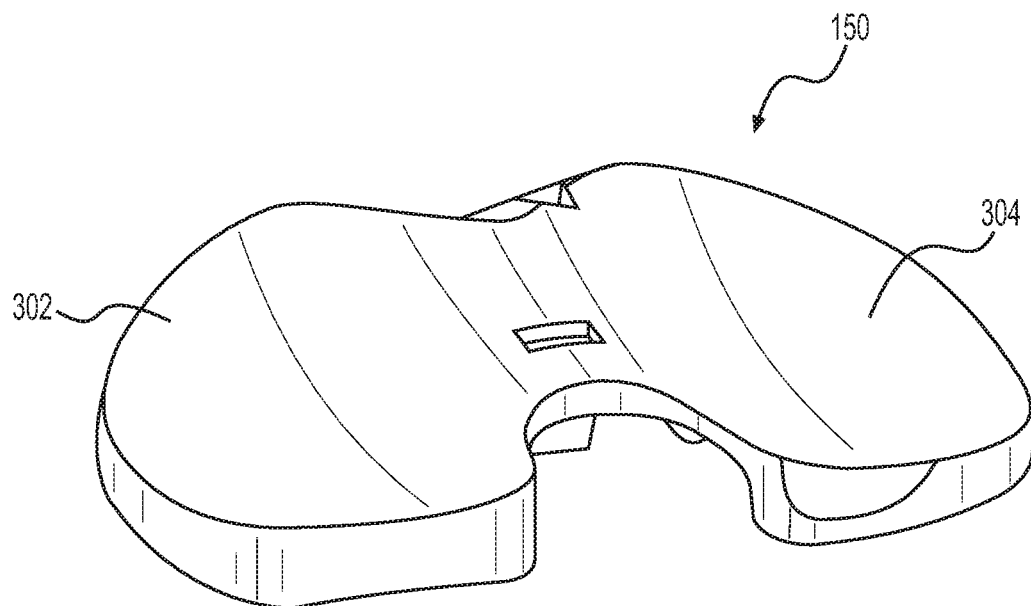
FIG. 8 is an illustration of a top view of a third shim in accordance with an example embodiment.

FIG. 8 is an illustration of a top view of shim 150 in accordance with an example embodiment. Shim 150 is a shim from plurality of shims 126 of the second type for a right knee joint. Shim 150 corresponds to shim 130 of plurality of shims 124 for the left knee joint. Shim 150 is used to illustrate structural elements that can be part of a shim from plurality of shims 126 or plurality of shims 124 of FIG. 1. A medial articular surface 302 and a lateral articular surface 304 is configured to couple to a femoral prosthetic component to support movement of the right knee joint. It should be noted that shim 150 is the thinnest shim of plurality of shims 150. In one embodiment, shim 150 and measurement module 180 of FIG. 1 has a height of 10 millimeters when coupled together.

Figure 9:
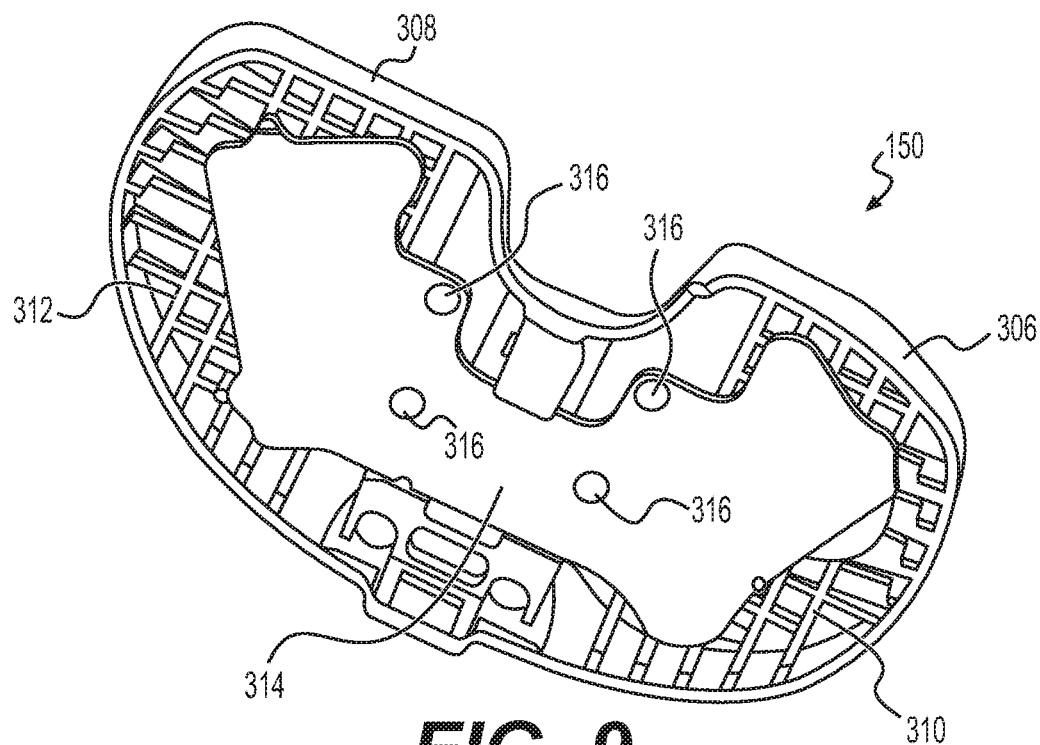
FIG. 9 is an illustration of a bottom view of the third shim in accordance with an example embodiment.

FIG. 9 is an illustration of a bottom view of shim 150 in accordance with an example embodiment. As stated previously, structural elements disclosed on shim 150 are used on at least one of plurality of shims 126 or at least one of plurality of shims 124 of FIG. 1. Shim 150 has a first plurality of columns coupled to medial articular surface 302 and a second plurality of columns coupled to lateral articular surface 304 of FIG. 8. The first plurality of columns and the second plurality of columns are similar to that shown in FIGS. 6 and 7 for shim 140. Shim 150 has a sidewall 308 on the medial side and a sidewall 306 on the lateral side. Shim 150 further includes structural webbing 312 and structural webbing 310 respectively underlying medial articular surface 302 and lateral articular surface 304 of FIG. 8. A plate 314 couples to the first plurality of columns and the second plurality of columns. In one embodiment, it has been found that structural webbing 310 and 312 does prevent flexing of shim 150 because the height of shim 150 reduces the depth of structural webbing 310 and 312 thereby reducing the resistance to flexing under loading by a leg. Flexing can introduce measurement error. In one embodiment, plate 314 is coupled to shim 150 to reduce flexing to increase measurement accuracy. In one embodiment, plate 314 is a rigid steel plate. Plate 314 can comprise a rigid polymer, metal, or metal alloy. Retaining features 316 couple to shim 150 to retain plate 314 to shim 150. In one embodiment, plate 314 couples to the first plurality of columns and the second plurality of columns that respectively couple to medial articular surface 302 and lateral articular surface 304 of shim 150 of FIG. 8. In one embodiment, retaining features 316 are rivets that can be glued or welded in place to retain plate 314 to shim 150. Plate 314 is configured to couple to medial surface 186 and lateral surface 188 on side 196 of measurement module 180 of FIG. 1.

Figure 10:
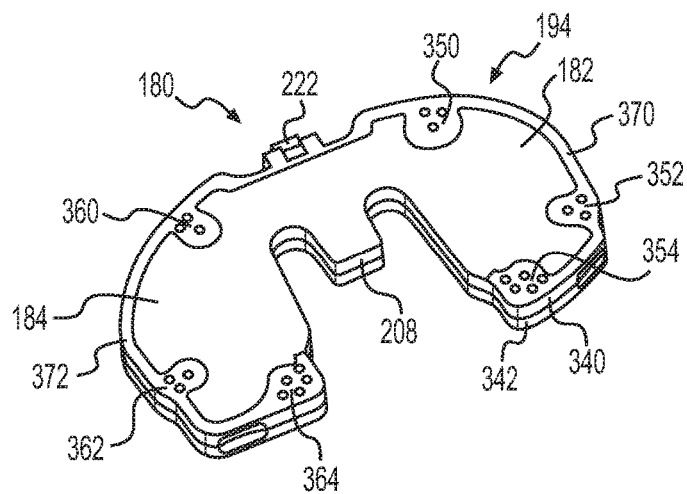
FIG. 10 is a top view of the measurement module in accordance with an example embodiment.

FIG. 10 is a top view of measurement module 180 in accordance with an example embodiment. Measurement module 180 comprises a support structure 340 and a support structure 342. Support structure 340 and 342 couple together to form a housing for electronic circuitry and a plurality of sensors. Support structure 340 includes a plurality of raised regions that extend above medial surface 182 and lateral surface 184. Medial surface 182 and lateral surface 184 of support structure 340 is configured to couple to one of the plurality of shims 124 which correspond to a left prosthetic knee joint. Referring briefly to FIGS. 2 and 7, columns 240, 242, and 244 couple to the medial articular surface 202 and columns 234, 236, and 238 couple to the lateral articular surface 204 of shim 140. As mentioned previously, columns 240, 242, and 244 are placed at the vertexes of a first triangle. Columns 234, 236, and 238 are placed at the vertexes of a second triangle. In one embodiment, columns 244, 242, and 240 respectively correspond to raised regions 350, 352, and 354 of support structure 340 such that columns 244 couples to raised region 350, column 242 couples to raised region 352, and column 240 couples to raised region 354 when shim 140 is coupled to measurement module 180. In one embodiment, columns 238, 236, and 234 correspond to raise regions 360, 362, and 364 such that column 238 couples to raised region 360, column 236 couples to raised region 362, and column 234 couples to raised region 364 when shim 140 is coupled to measurement module 180. In general, raised regions 350, 352, and 354 or raised regions 360, 362, and 364 support coupling a load applied to a medial or a lateral articular surface of a shim of the first type to vertexes of a polygon in both the shim and measurement module 180. In one embodiment, raised regions 350, 352, and 354 are considered part of medial surface 182. Similarly, raised regions 360, 362, and 364 are considered part of lateral surface 184. Raised regions 350, 352, and 354 and raised regions 360, 362, and 364 comprise strengthened regions of support structure 340 to handle loading applied by the musculoskeletal system and to minimize flexing. In one embodiment, substantially all of the load applied to the medial and lateral articular surfaces of a shim are coupled through the plurality of columns, to the raised regions on support structure 340, and finally compressing force, pressure, or load sensors underlying each raised region of measurement module 180. The measurement data A peripheral raised region 370 is formed around a periphery on the medial side 182 of support structure 340. Similarly, a peripheral raised region 372 is formed around a periphery on the lateral side 184 of support structure 340. Peripheral raised region 370 couples to raised regions 350, 352, and 354. Peripheral raised region 372 couples to raised regions 360, 362, and 364. In one embodiment, peripheral raised regions 370 and 372 have a same height as raised regions 350, 352, 354, 360, 362, and 364. In one embodiment, peripheral raised regions 370, 372 and raised regions 350, 352, 354, 360, 362, and 364 are reinforced with more material to strengthen those areas. Peripheral raised regions 370 and 372 coupled between raised regions 350, 352, 354, 360, 362, and 364 strengthen support structure 340 to increase rigidity of the raised regions and reduce flexing.

Figure 11:
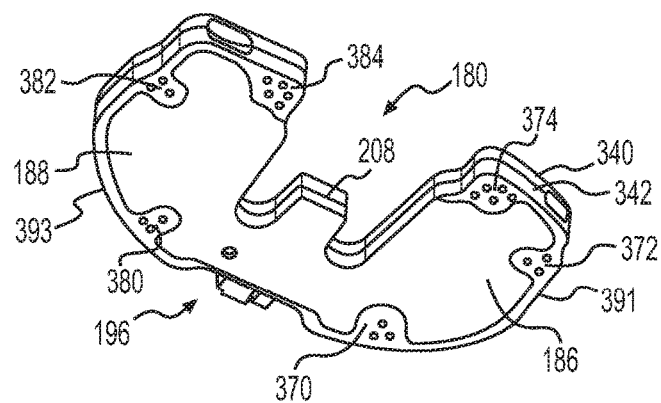
FIG. 11 is a bottom view of the measurement module in accordance with an example embodiment.

FIG. 11 is a bottom view of measurement module 180 in accordance with an example embodiment. Measurement module 180 comprises a support structure 340 and a support structure 342. Support structure 342 includes a plurality of raised regions that extend above medial surface 186 and lateral surface 188 configured to couple to a shim of the second type for a right prosthetic knee joint. In one embodiment, the plurality of raised regions correspond to the vertexes of a polygon defined by the plurality of columns coupled the medial articular surface and the lateral articular surface of a shim for a right prosthetic knee joint. In one embodiment, raised regions 370, 372, and 374 are at vertexes of a first triangle corresponding to a plurality of columns coupled to medial articular surface 210 of shim 160 of FIG. 3. Similarly, raised regions 380, 382, and 384 correspond to a plurality of columns at vertexes of a second triangle coupled to lateral articular surface 212 of shim 160 of FIG. 3. In general, each shim of plurality of shims 126 will have a first plurality of columns and a second plurality of columns respectively coupled to a medial articular surface and a lateral articular surface. Although the not shown, the first plurality of columns and the second plurality of columns for each shim of plurality of shims 126 are similar to that shown in FIG. 7 for shim 140 for a left prosthetic knee joint. In one embodiment, the first plurality of columns of a shim from plurality of shims 126 of FIG. 1 couple to raised regions 370, 372, and 374 of measurement module 180 and the second plurality of columns of the shim from plurality of shims 126 couples to raised regions 380, 382, and 384 when the shim is coupled to measurement module 180. Thus, the load applied to the medial articular surface and the lateral articular surface of the shim of the second type is respectively coupled to raised regions 370, 372, and 374 and raised regions 380, 382, and 384 via a first plurality of columns and a second plurality of columns extending from the shim. The first plurality of columns are placed at vertexes of a first polygon. Similarly, the second plurality of columns are placed at vertexes of a second polygon. Raised regions 370, 372, and 374 and raised regions 380, 382, and 384 comprise strengthened regions of support structure 342 that support loading applied by the musculoskeletal system to the shim and measurement module 180 without flexing or distorting.

A peripheral raised region 391 is formed around a periphery on the medial side 186 of support structure 342. Similarly, a peripheral raised region 393 is formed around a periphery on the lateral side 188 of support structure 342. Peripheral raised region 391 couples to raised regions 370, 372, and 374. Peripheral raised region 393 couples to raised regions 380, 382, and 384. In one embodiment, peripheral raised regions 391 and 393 have a same height as raised regions 370, 372, 374, 380, 382, and 384. In one embodiment, peripheral raised regions 391, 393 and raised regions 370, 372, 374, 380, 382, and 384 are reinforced with more material to strengthen those areas. Peripheral raised regions 391 and 393 coupled between raised regions 370, 372, 374, 380, 382, and 384 strengthen support structure 342 to increase rigidity of the raised regions and reduce flexing.

Figure 12:
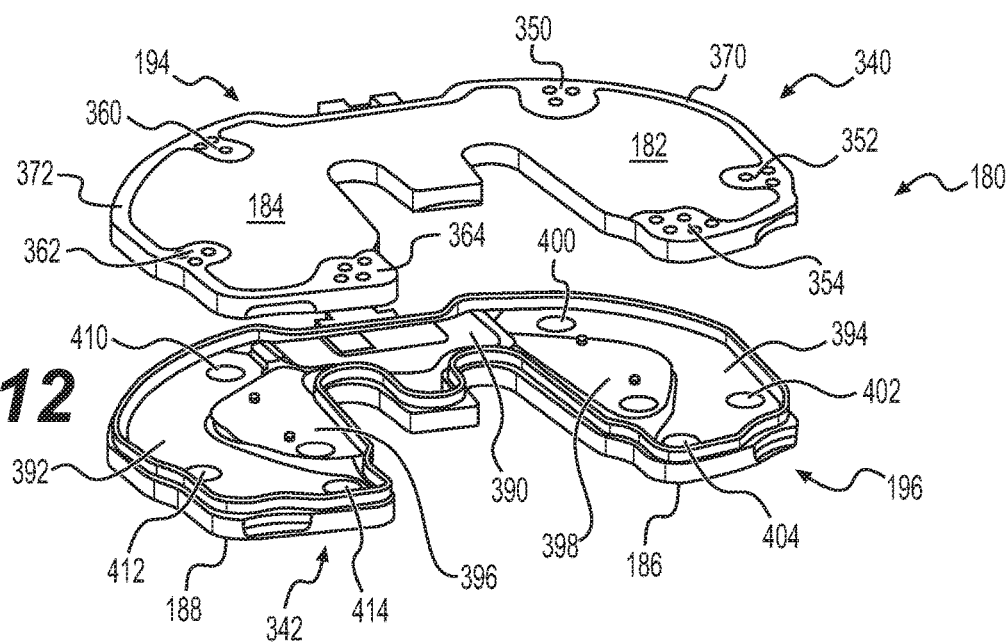
FIG. 12 is an exploded view of a first support structure and a second support structure of the measurement module in accordance with an example embodiment.

FIG. 12 is an exploded view of support structure 340 and support structure 342 in accordance with an example embodiment. Support structures 340 and 342 form a housing for electronic circuitry 390 and at least one sensor to form measurement module 180. The top view of support structure 340 illustrates raised regions 350, 352, and 354 on medial surface 182 and raised regions 360, 362, and 364 on lateral surface 184 of support structure 340. In one embodiment, support structure 342 includes one or more cavities to place sensors and electronic circuitry 390. Electronic circuitry 390 is configured to control a measurement process and to transmit measurement data from measurement module 180 to computer 110 as shown in FIG. 1. Electronic circuitry 390 is located between sensors 400, 402, and 404 on the medial side and sensors 410, 412, and 414 on the lateral side of support structure 342. In one embodiment, electronic circuitry is placed in an unloaded or lightly loaded portion of measurement module 180. Electronic circuitry 390 can be mounted on and interconnected on a printed circuit board to form a circuit or system. In one embodiment, the printed circuit board has multiple layers of interconnect to form the circuit or system. Sensors 400, 402, and 404 are coupled to electronic circuitry 390 through a flexible interconnect 394 on the medial side of support structure 342. Similarly, flexible interconnect 392 couples electronic circuitry 390 to sensors 410, 412, and 414. In one embodiment, sensors 400, 402, 404, 410, 412, and 414 can be integrated within the interconnect 392 and 394. Sensor integration supports improved sensor matching and reduces variation in performance characteristics of the sensors over different conditions such as time or temperature. In one embodiment, interconnect 392 and 394 can also include shielding for the sensors and shielding of the interconnect coupling the sensors to electronic circuitry 390. Shielding reduces parasitic capacitance from affecting the sensors. Shielding also reduces the pickup of stray signals that could affect a measurement value. Alternatively, sensors 400, 402, 404, 410, 412, and 414 can also be discrete devices that couple to interconnect 392 and 394. In one embodiment sensors 400, 402, 404, 410, 412, and 414 can be capacitive, piezo, or MEMs load sensors.

Load sensors 400, 402, and 404 respectively align to raised regions 350, 352, and 354 of support structure 340. Load sensors 400, 402, and 404 respectively align to raised region 370, 372, and 374 of support structure 342 of FIG. 11. In other words, load sensors 400, 402, and 404 respectively couple between raised regions 350, 352, 354 of support structure 340 and raised regions 370, 372, and 374 of support structure 342. Similarly, load sensors 410, 412, and 414 respectively align to raised regions 360, 362, and 364 of support structure 340. Load sensors 410, 412, and 414 respectively align to raised regions 380, 382, and 384 of support structure 342 of FIG. 11. Thus, load sensors 410, 412, and 414 respectively couple between raised regions 360, 362, 364 of support structure 340 and raised regions 380, 382, and 384 of support structure 342.

An interconnect 398 couples a first power source to electronic circuitry 390 on the medial side of support structure 342. Similarly, an interconnect 396 couples a second power source to electronic circuitry 390 on the lateral side of support structure 342. The first power source resides between a portion of medial surfaces 182 and 186 respectively of support structures 340 and 342. The second power source resides between a portion of lateral surfaces 184 and 188 respectively of support structures 340 and 342. The first and second power sources provide power to measurement module 180 during a surgery. The first and second power sources can be a battery, inductor, capacitor, or other power source. In one embodiment, loading applied to measurement module does not compress the first or second power sources as the load is delivered through columns of a shim coupling to raised regions on the measurement module. Interconnect 396 and 398 can be flexible and soldered to the printed circuit board to which electronic circuitry 390 is mounted.

Figure 13:
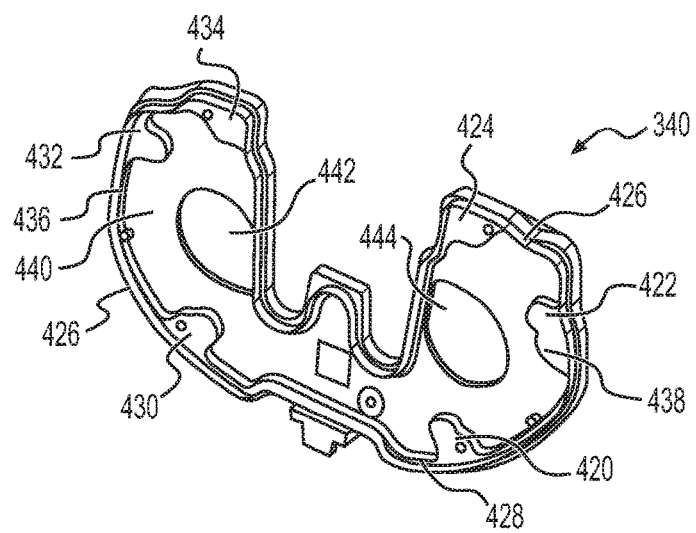
FIG. 13 is an illustration of an interior of the first support structure of the measurement module in accordance with an example embodiment.

FIG. 13 is an illustration of an interior of support structure 340 of measurement module 180 of FIG. 10 in accordance with an example embodiment. The interior of support structure 340 has a medial interior surface 438 and a lateral interior surface 440. Raised regions 420, 422, and 424 are formed on medial interior surface 438. Raised regions 420, 422, and 424 respectively align to raised regions 350, 352, and 354 of FIG. 10. A peripheral raised region 428 is formed on a periphery of medial interior surface 438. In one embodiment, the peripheral raise region 428 couples to raised regions 420, 422, and 424. Support structure 340 can comprise a polymer such as polyurethane, PEEK, polycarbonate, or other medically approved plastics. Alternatively, support structure 340 can comprise a metal, metal alloy, or a composite material.

Loading applied to the articular surface of a shim is transferred to raised regions of medial surface 182 or lateral surface 184. The raised regions are placed at vertexes of a polygon on medial surface 182 or lateral surface 184. Thus, the load applied to the articular surfaces of the shim is transferred to predetermined locations on measurement module 180 for a left prosthetic knee joint. The predetermined locations of the raised regions and the load magnitudes measured at each raised regions are used by computer 110 to calculate the contact point and load magnitude where the femoral component couples to medial surface 182 or lateral surface 184 in real-time. In one embodiment, the raised regions support coupling at predetermined points as the other portions of medial surface 182 or lateral surface 184 are at a different height. It is of benefit to review a predetermined location or single vertex of support structure 340 or support structure 342 of measurement module 180 as they are all similar. In the example, a predetermined or single vertex of a polygon on measurement module 180 corresponds to raised region 350 on medial surface 182 of FIG. 10 and raised region 420 on medial interior surface 438. Raised region 350 and raised region 420 are respectively coupled to other raised regions by peripheral raised region 370 and peripheral raised region 428. The combined thickness of the polymer material at the predetermined location or single vertex of a polygon at raised regions 350 and 420 are such that a column of a shim transfers the load substantially equally across the surface of raised region 350. Raised region 420 then transfers the load substantially equally across a load sensor to which it couples. Each predetermined location or vertex of measurement module 180 operates similarly. In general, the added thickness of the material at the raised regions of measurement module is rigid under loading to prevent flexing and to distribute the load across the entire sensor surface equally. In one embodiment, the raised regions such as raised regions 350 and 420 that respectively couples to a column of a shim or a sensor has an area larger than or equal to the area of the column or sensor. A cavity 444 is formed in medial interior surface 438 to provide space to prevent support structure 340 from coupling to a power source when loading is applied to a shim coupled to measurement module 180.

Raised regions 430, 432, and 434 are formed on lateral interior surface 440. Raised regions 430, 432, and 434 respectively align to raised regions 360, 362, and 364 of FIG. 10. A peripheral raised region 436 is formed on a periphery of lateral interior surface 440. In one embodiment, the peripheral raise region 440 couples to raised regions 430, 432, and 434. A further example of the material at a vertex of a polygon comprises raised region 430, support structure 340, and raised region 360. The combined thickness of the polymer material at the vertex of the polygon as disclosed herein above is such that when loaded by a column of a shim delivers the load substantially equal across the surface of a load sensor to which raised region 430, support structure 340, and raise region 360 couples. The material at the vertex of the polygon is rigid to prevent flexing under load. Furthermore, the added material provided by peripheral raised region 436 has been found to further reduce flexing at each vertex on lateral interior surface 440 to support accurate measurement at each vertex where the loading is applied to each load sensor by a corresponding column. A cavity 442 is formed in lateral interior surface 440 to provide space to prevent support structure 340 from coupling to a power source when loading is applied to a shim coupled to measurement module 180. A tongue 426 couples circumferentially around a perimeter on an internal side of support structure 340. Tongue 426 is configured to couple to a corresponding glue channel in support structure 342 of FIG. 10. In one embodiment, glue is placed within the glue channel and tongue 426 fits within the glue channel to seal and retain support structure 340 to support structure 342 as shown in FIG. 10.

Figure 14:
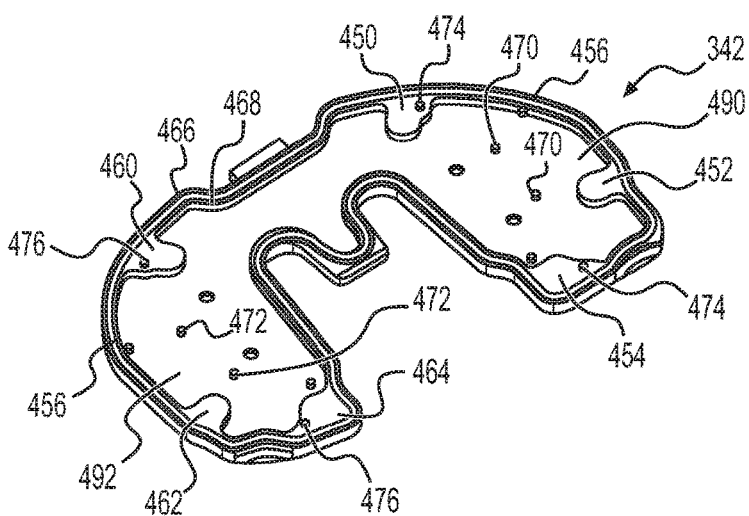
FIG. 14 is an illustration of an interior of the second support structure of the measurement module in accordance with an example embodiment.

FIG. 14 is an illustration of an interior of support structure 342 of measurement module 180 of FIG. 10 in accordance with an example embodiment. The interior of support structure 342 has a medial interior surface 490 and a lateral interior surface 492. Medial interior surface 490 and lateral interior surface 492 respectively face medial interior surface 438 and lateral interior surface 440 in FIG. 13 when support structure 342 couples to support structure 340. Raised regions 450, 452, and 454 are formed on medial interior surface 490 and are raised above medial interior surface 490. Similarly, raised regions 460, 462, and 464 on lateral interior surface 492 are raised above lateral interior surface 492. Raised regions 450, 452, and 454 respectively align to raised regions 420, 422, and 424 of FIG. 13 when support structure 340 is coupled to support structure 342. Raised regions 460, 462, and 464 respectively align to raised regions 430, 432, and 434 of support structure 342 of FIG. 13. A glue channel 456 is formed by walls 466 and 468 around the interior periphery of support structure 342. A tongue 426 on support structure 340 of FIG. 13 is configured to fit within glue channel 456 of support structure 342. Glue channel 456 holds glue to adhere tongue 426 of support structure 340 of FIG. 13 to glue channel 456. A peripheral raised region of support structure 342 comprises wall 466, tongue 426, and wall 468 when support structure 340 is glued to support structure 342. The peripheral raised region surrounds medial interior surface 490 and lateral interior surface 492. The peripheral raise region of support structure 342 couples to raised regions 450, 452, 454, 460, 462, and 464 when support structure 340 is coupled to support structure 342. As mentioned previously, support structure 342 can comprise a metal, a metal alloy, or a polymer such as polyurethane, PEEK, polycarbonate, or other medically approved plastics.

An example of the material at a vertex of a polygon for measuring load magnitude on the medial side comprises raised region 350 (FIG. 10), raised region 420 (FIG. 13), raised region 450 (FIG. 14), and raised region 370 (FIG. 11). A load sensor is placed between raised region 420 of FIG. 13 and raised region 450 of FIG. 14. Loading applied at the vertex compresses the load sensor. The combined thickness of the polymer material at the vertex of the polygon is such that when loaded by a column of a shim delivers the load substantially equal across the surface of a load sensor to which it couples. The material at the vertex of the polygon is rigid to prevent flexing under load. Furthermore, the added material provided by the peripheral raised region of support structure 342 comprising glue channel 456 in combination with tongue 426 of FIG. 13 has been found to further reduce flexing at each vertex to support accurate measurement at each vertex where the loading is applied to each load sensor by a corresponding column. Medial interior surface further includes alignment and retaining features 470 and alignment and retaining features 474 configured to support alignment of flexible interconnect.

As mentioned previously raised regions 460, 462, and 464 are formed on and above lateral interior surface 492. Raised regions 460, 462, and 464 respectively align to raised regions 430, 432, and 434 of support structure 340 of FIG. 13 when support structure 340 couples to support structure 342. Raised regions 460, 462, and 464 also respectively align to raised regions 380, 382, and 384 of support structure 342 of FIG. 11. An example of the material at a vertex of a polygon for measuring load magnitude on the lateral side comprises raised region 360 (FIG. 10), raised region 430 (FIG. 13), raised region 460 (FIG. 14), and raised region 380 (FIG. 11). A load sensor is placed between raised region 430 of FIG. 13 and raised region 460 of FIG. 14. Loading applied at the vertex compresses the load sensor on the lateral side. The combined thickness of the polymer material at the vertex of the polygon is such that when loaded by a column of a shim delivers the load substantially equal across the surface of a load sensor to which it couples as disclosed on the medial side herein above. The material at the vertex of the polygon is rigid to prevent flexing under load. Furthermore, the added material provided by the peripheral raised region of support structure 342 comprising glue channel 456 in combination with tongue 426 of FIG. 13 has been found to further reduce flexing at each vertex to support accurate measurement at each vertex where the loading is applied to each load sensor by a corresponding column. Lateral interior surface further includes alignment and retaining features 472 and alignment and retaining features 476 configured to couple to and retain flexible interconnect.

Figure 15:
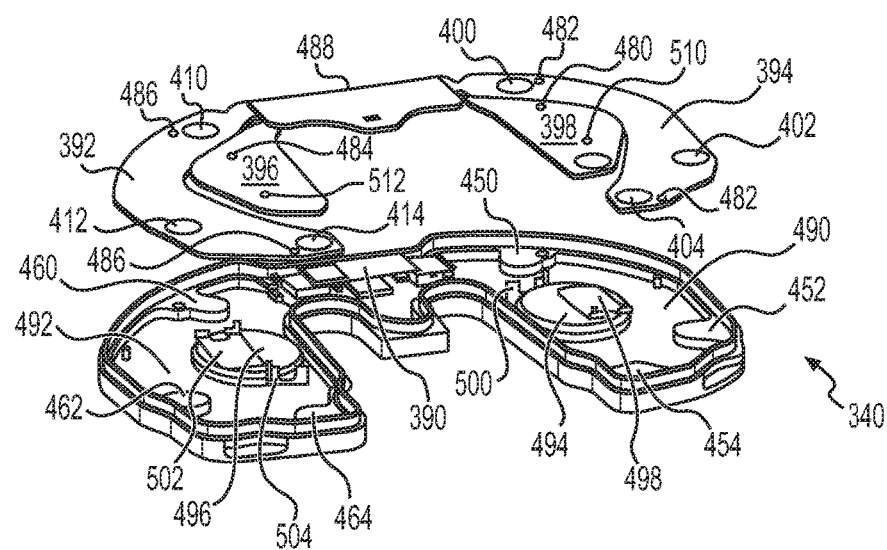
FIG. 15 is an illustration of electronic circuitry in the measurement module in accordance with and example embodiment.

FIG. 15 is an illustration of electronic circuitry 390 in accordance with and example embodiment. Electronic circuitry 390 is housed in measurement module 180 and is configured to control a measurement process and to transmit measurement data. In one embodiment, electronic circuitry 390 is illustrated as a plurality of electronic components. In one embodiment, electronic circuitry 390 is configured mount to printed circuit board and the electronic components are configured to be interconnected by printed circuit board 488. Printed circuit board 488 includes one or more layers of interconnect for interconnecting electronic circuitry 390 to form a circuit or a system. Flexible interconnect 398 and 394 couple to printed circuit board 488 from a medial side of measurement module 180. Similarly, flexible interconnect 392 and 396 couple to printed circuit board 488 from a lateral side of measurement module 180. In one embodiment, electronic circuitry 390 is placed in an unloaded region of measurement module 180 between the lateral and medial sides. In one embodiment, flexible interconnect 392, 394, 396, and 398 can be solder bumped to printed circuit board 488 for interconnectivity. At least one sensor couples to electronic circuitry 390. The at least one sensor is configured to measure a parameter.

The assembled measurement module 180 of FIG. 10 is configured to measure loading applied to a medial and lateral articular surface of a shim of the first type (e.g. left prosthetic knee joint) or the second type (e.g. right prosthetic knee joint). Sensors are housed within measurement module 180 to measure a load magnitude and a position of load applied to the medial and lateral articular surface by the prosthetic knee joint. In one embodiment, sensors can be integrated into flexible interconnect 392 and 394 at predetermined locations. Alternatively, sensors can be coupled to flexible interconnect 392 and 394 at the predetermined locations. In the example, sensors are placed at vertexes of a polygon. As shown, the sensors are placed at the vertexes of a triangle on the medial side and the lateral side of measurement module 180. More specifically, sensors 400, 402, and 404 respectively couple between raised regions 450, 452, and 454 on support structure 342 and raised regions 420, 422, and 424 on support structure 340 as shown in FIG. 13. The predetermined locations of sensors 400, 402, and 404 on the medial side of measurement module 180 correspond to the medial surfaces 182 and 186 respectively shown in FIG. 10 and FIG. 11. The predetermined locations also translate to the medial surface of a shim coupled to measurement module 180.

Similarly, sensors 410, 412, and 414 are placed at vertexes of a triangle on the lateral side of measurement. The vertexes on the lateral side can differ from the vertexes on the medial side such that a triangle formed by the vertexes on the lateral side will differ in shape, area, or geometry from a triangle formed by the vertexes on the medial side of measurement module 180. In one embodiment, measurement module 180 is non-symmetrical about the anterior-posterior axis. More specifically, sensors 410, 412, and 414 respectively couple between raised regions 460, 462, and 464 on support structure 342 and raised regions 430, 432, and 434 on support structure 340 as shown in FIG. 13. The predetermined locations of sensors 400, 402, and 404 on the lateral side of measurement module 180 correspond to the medial surfaces 184 and 188 respectively shown in FIG. 10 and FIG. 11. The predetermined locations also translate to the lateral surface of a shim coupled to measurement module 180.

In one embodiment, at least one retaining feature extends from medial interior surface 490. The at least one retaining feature couples through an opening in flexible interconnect 394. The at least one retaining feature aligns and retains sensors 400, 402, and 404 to raised regions 450, 452, and 454 of support structure 342 and raised regions 420, 422, and 424 of support structure 340 of FIG. 13. In the example, two retaining features 474 as shown in FIG. 14 extend from support structure 342 to couple through openings 482 of flexible interconnect 394. Similarly, at least one retaining at least one retaining feature extends from lateral surface 492. The at least one retaining feature from lateral surface 492 couples through an opening in flexible interconnect 392. The at least one retaining feature aligns and retains sensors 410, 412, and 414 to raised regions 460, 462, and 464 of support structure 342 and raised regions 430, 432, and 434 of support structure 340 of FIG. 13. In the example, two retaining features 476 as shown in FIG. 14 extend from support structure 342 to couple through openings 486 of flexible interconnect 392.

Flexible interconnect 398 and flexible interconnect 396 are configured to respectively couple to power source 494 and power source 496. Power sources 494 and 496 are configured to power measurement module 180 for a prosthetic knee implant operation. Power sources 494 and 496 can be capacitors, inductors, an active power source, or other energy storage devices. In the example, power source 494 and power source 496 are batteries that are configured to not be recharged as measurement module is a disposable device after the surgery is completed. A terminal 498 and a terminal 500 respectively couples to a first electrode and a second electrode of power source 494. Terminals 500 and 498 have a retaining feature to couple and align flexible interconnect 398 to power source 494. In the example, terminals 500 and 498 each have a retaining feature respectively to couple through opening 480 and opening 510 of flexible interconnect 398. Similarly, a terminal 504 couples to a first electrode of power source 496 and a terminal 502 couples to a second electrode of power source 496. Terminals 504 and 502 have a retaining feature to couple and align flexible interconnect 396 to power source 496. In one embodiment, terminals 498, 500, 502, and 504 have pins that respectively couple through openings 510, 480, 484, and 512. In the example, terminals 504 and 502 each have a retaining feature respectively to couple through opening 512 and opening 484 of flexible interconnect 396. In one embodiment, terminals 500, 494, 504, and 502 and flexible interconnect 396 and 398 provide a low resistance path to couple power sources 496 and 494 to electronic circuitry 390 and printed circuit board 488. In one embodiment, flexible interconnect 396 and 398 configure power sources 496 and 494 in a series configuration. Alternatively, flexible interconnect 396 and 398 can couple power sources 496 and 494 in parallel if required.

The measurement data from sensors 400, 402, 404, 410, 412, and 414 is used to determine a load magnitude applied to a medial articular surface and a lateral articular surface of a shim coupled to measurement module 180. The measurement data and the predetermined locations of the sensors/raised regions can be used to determine a location of applied load on the medial articular surface or the lateral articular surface of the shim coupled to measurement module 180 by geometry and load magnitudes measured by each sensor.

Figure 16:
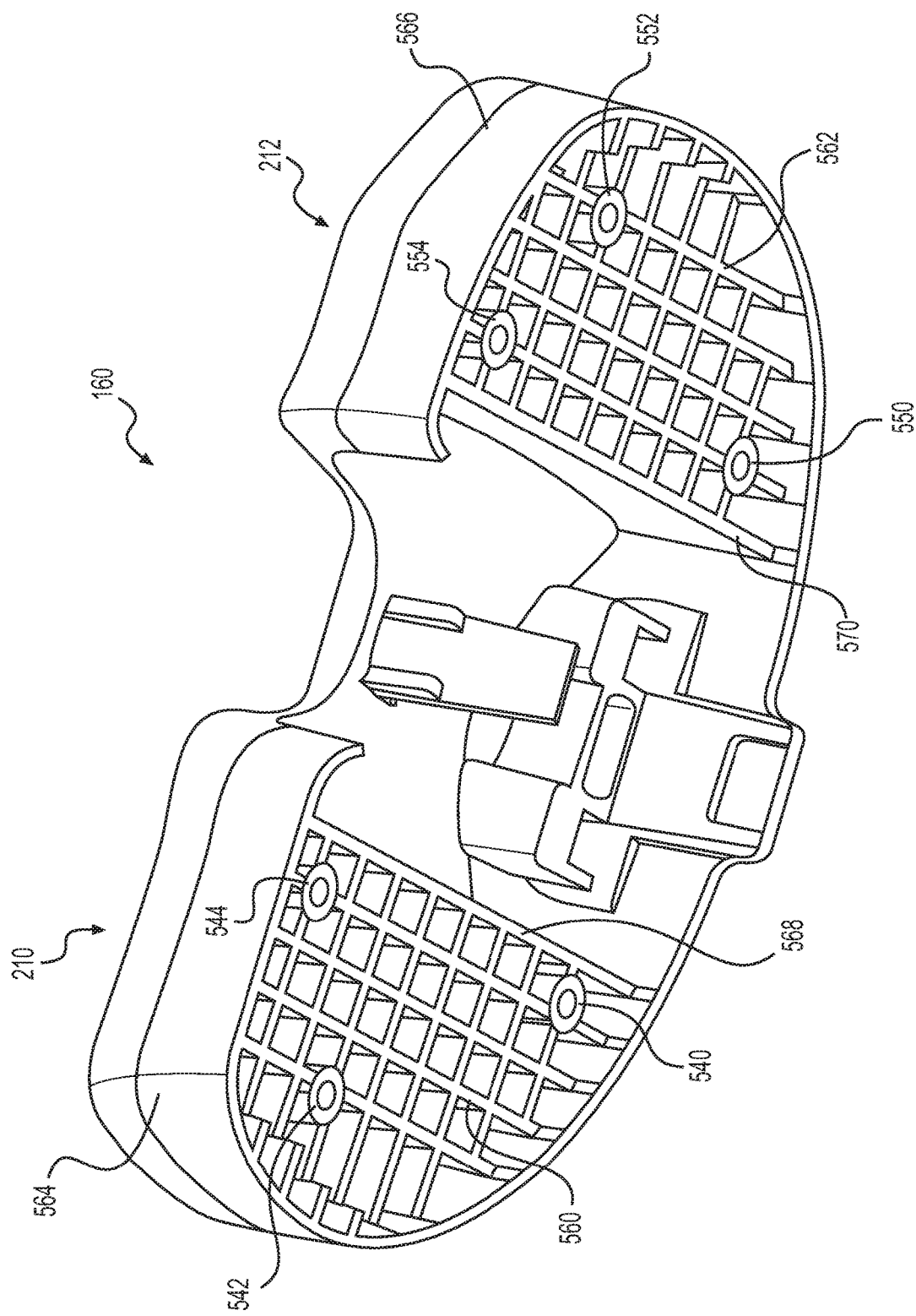
FIG. 16 is a bottom view of the second shim in accordance with an example embodiment.

FIG. 16 is a bottom view of shim 160 in accordance with an example embodiment. Although, shim 160 is disclosed, the structural elements described relate to shims 124 of the first type and shims 126 of the second type of FIG. 1. Shim 160 has medial articular surface 210 and lateral articular surface 212. A plurality of columns couple to medial articular surface 210. Similarly, a plurality of columns couple to lateral articular surface 212. The plurality of columns that couple to the medial or lateral articular surface are placed at vertexes of a polygon. In one embodiment, columns 540, 542, and 544 couple to medial articular surface 210 defining a first triangle. Similarly, columns 550, 552, and 554 couple to lateral articular surface 212 defining a second triangle. In on embodiment, the first triangle defined by columns 540, 542, and 544 corresponds to a first measurement area on medial articular surface 210. In one embodiment, the second triangle defined by columns 550, 552, and 554 corresponds to a second measurement area on lateral articular surface 212. In one embodiment, the first triangle or the second triangle has respectively less area than medial articular surface 210 or the lateral articular surface 212 of FIG. 2. In one embodiment, medial articular surface 210 of shim 160 differs in area, contour, or shape from lateral articular surface 212 of shim 160. Similarly, the first triangle defined by columns 540, 542, and 544 can differ by area or shape from the second triangle defined by columns 550, 552, and 554.

In general, the first or second triangles of shim 160 are a subset respectively of medial articular surface 210 and lateral articular surface 212. A medial condyle and a lateral condyle of the femoral prosthetic component respectively couples to medial articular surface 210 and lateral articular surface 212 of shim 160. In one embodiment, the contact point of the medial or lateral condyle of the femoral prosthetic component respectively couples within the first or second triangle areas over the range of motion of shim 160. In one embodiment, the alignment, stability, and long-term reliability of the prosthetic joint coupling to the musculoskeletal system could be compromised if a contact point is outside the polygon defined by columns of the shim thereby reducing reliability or increasing wear of the prosthetic joint.

A structural webbing 560 and 562 is respectively placed within an interior medial cavity and an interior lateral cavity of shim 160. Structural webbing 560 and 562 stiffens shim 160 and reduces flexing of shim 150 under loading by the musculoskeletal system. Structural webbing 560 couples between a sidewall 564 of shim 160 and columns 540, 542, and 544. Structural webbing 562 also couples between columns 540, 542, and 544. In one embodiment, structural webbing 560 couples between an internal wall 568 and columns 540, 542, and 544. Structural webbing 560 can also couple between sidewall 564 and internal wall 568. Structural webbing 560 also prevents the flexing of columns 540, 542, and 544. Similarly, structural webbing 562 couples between a sidewall 566 of shim 160 and columns 550, 552, and 554. In one embodiment, structural webbing 562 couples between an internal wall 570 and columns 550, 552, and 544. Structural webbing 562 can also couple between sidewall 566 and internal wall 570. Structural webbing prevents flexing of columns 550, 552, and 554 on the lateral side of shim 160.

In one embodiment, columns 540, 542, and 544 respectively extend past structural webbing 560 to couple to medial surface 186 of measurement module 180 as shown in FIG. 2. In one embodiment, structural webbing 560 does not couple to medial surface 186 of measurement module 180 of FIGS. 2 and 3. Columns 550, 552, and 554 extend past structural webbing 562 such that columns 550, 552, and 554 couple to lateral surface 188 of measurement module 180 of FIG. 2 when shim 140 is coupled to measurement module 180 of FIG. 3. In one embodiment, structural webbing 562 does not couple to lateral surface 188 when shim 160 is coupled to measurement module 180. In general, columns 540, 542, and 544 couple loading applied to shim 160 to measurement module 180 on the medial side. Columns 550, 552, and 554 couple loading applied to shim 160 on the lateral side.

Shim 160 of plurality of shims 126 as shown in FIG. 1 couples to measurement module 180 with the second side having medial surface 186 and lateral surface 188 facing and coupling to shim 160 as shown in FIG. 2. In general, loading applied to medial articular surface 210 and lateral articular surface 212 of shim 160 is coupled from the predetermined locations of the columns in relation to the corresponding surface to predetermined locations on measurement module 180 as shown in FIG. 3. In one embodiment, substantially all of the loading is applied through the columns on the medial and lateral sides of the shim to measurement module 180. In one embodiment, correction can be applied to a program for calculating load magnitude at each predetermined position on the medial and lateral articular surfaces for quantifiable losses in transferring load. In the example, columns 540, 542, and 544 couple to predetermined locations on medial surface 186 of measurement module 180. In particular, columns 540, 542, and 544 respectively couple to raised regions 370, 372, and 374 at the predetermined locations as shown in FIG. 11. Similarly, columns 550, 552, and 554 couple to predetermined locations on lateral surface 188 of measurement module 180. In particular, columns 550, 552, and 554 couple respectively couple to raised regions 380, 382, and 384 at the predetermined locations as shown in FIG. 11. Sensors 400, 402, and 404 respectively underlie raised regions 370, 372, and 374 of medial surface 186 as shown in FIG. 12. Sensors 410, 412, and 414 underlie raised regions 380, 382, and 384 of lateral surface 188 as shown in FIG. 12. Loading applied to shim 160 compresses sensors 400, 402, and 400 on the medial side and sensors 410, 412, and 414 on the lateral side of measurement module 180 that supports generating a load magnitude of applied force to medial articular surface 210 and lateral articular surface 212 of shim 160. Furthermore, each load magnitude corresponding to medial articular surface 210 and lateral articular surface 212 provided to computer 110 of FIG. 1 is used to calculate a contact point of a medial femoral condyle and a lateral femoral condyle respectively on medial articular surface 210 and lateral articular surface 212 of shim 160 based on the predetermined locations and load magnitudes. In one embodiment, the contact points and load magnitudes are reported in real-time on display 112 of computer 110 as shown in FIG. 1.

Figure 17:
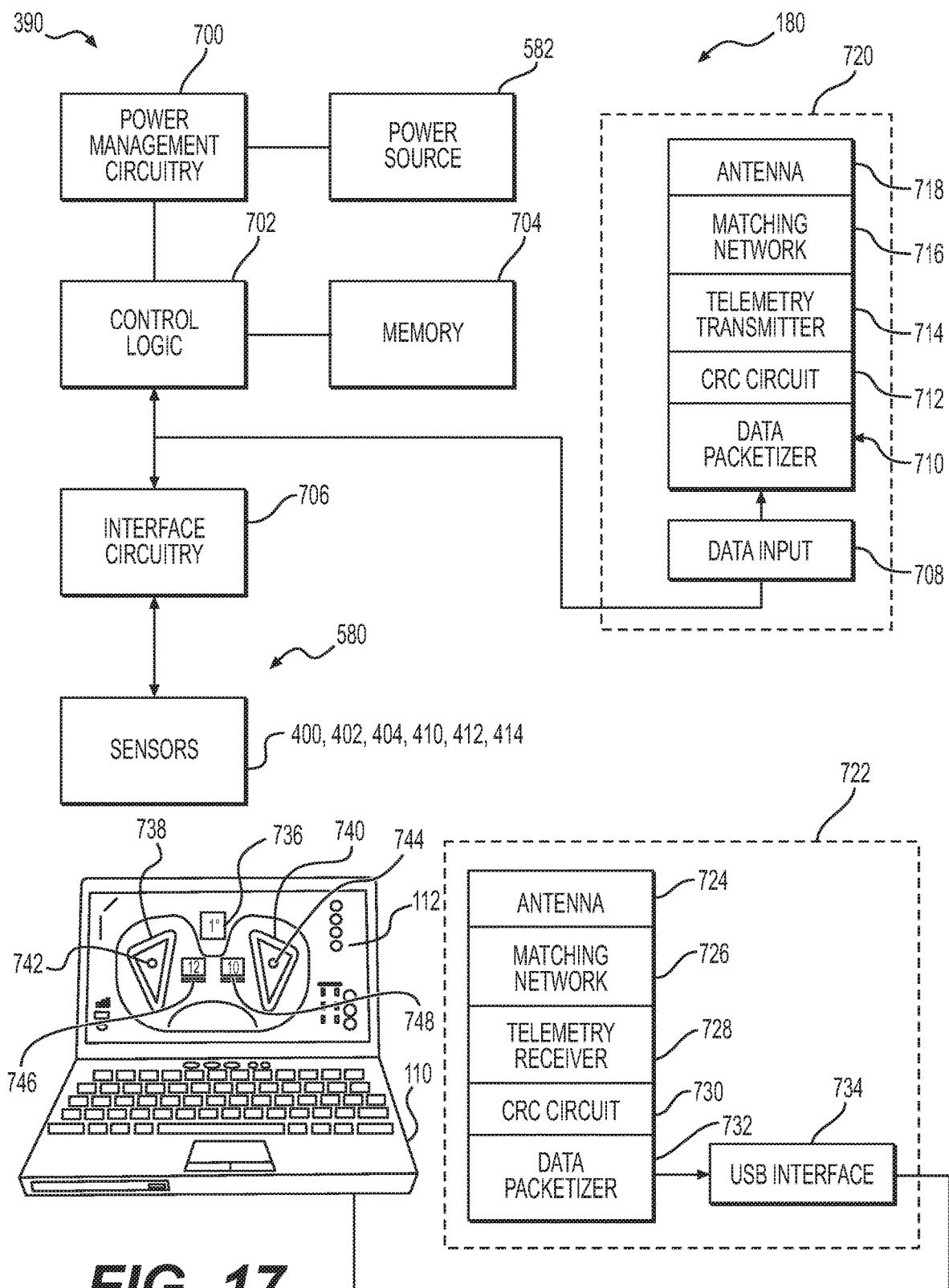
FIG. 17 is a block diagram of the electronic circuitry in the measurement module in accordance with an example embodiment.

FIG. 17 is a block diagram of electronic circuitry 390 in measurement module 180 as shown in FIG. 12 in accordance with an example embodiment. Electronic circuitry 390 couples to sensors 580. In general, sensors 580 comprises a tracking system configured to measure one or more parameters related to the musculoskeletal system or in proximity to the musculoskeletal system. For example, sensors 580 can comprise sensors to measure, position, slope, rotation, infection, bone density, adhesive sensing, pain, contact point, alignment, color, turbidity, viscosity, photo detection, images, movement, chemicals, sound, and loading to name but a few. In the example, sensors 580 comprise at least load sensors 400, 402, 404, 410, 412, and 414 in measurement module 180. Electronic circuitry 390 is configured to control a measurement process, receive measurement data from all sensors, and transmit the measurement data to computer 110 of FIG. 1 for further analysis and feedback. One or more parameters are measured by sensors 580 coupled to electronic circuitry 390 in measurement module 180 when coupled to a shim and inserted into a prosthetic knee joint. In the example, electronic circuitry 390 would receive measurement data from sensors 400, 402, and 404 for measurement of load applied at three predetermined locations on to the medial side a shim and measurement module 180 and sensors 410, 412, and 414 for measurement of load applied at three predetermined locations on the lateral side of the shim and measurement module 180. Computer 110 can have a GUI and provide measurement data in a visual, audible, or haptic form that supports rapid assimilation of the data as shown on display 112 of computer 110. Electronic circuitry 390 comprises power management circuitry 700, control logic 702, memory 704, interface circuitry 706 and wireless communication circuitry 720. A power source 582 couples to electronic circuitry 390 to power a measurement process. In one embodiment, power source 582 comprises power sources 494 and 496 as shown in FIG. 15. Electronic circuitry 390 has a small form factor such that it can be positioned on or within, or engaged with, or attached or affixed to or within, a wide range of physical systems including, but not limited to instruments, equipment, devices, prosthetic components, or other physical systems for use on or in human bodies and configured for sensing and communicating parameters of interest in real time.

In general, electronic circuitry 390 is configured to provide two-way communication between measurement module 180 and computer 110. As previously mentioned, measurement module 180 can be adapted for use in or on the musculoskeletal system, a prosthetic system, orthopedic equipment, or an orthopedic tool. In one embodiment, measurement module 180 provides quantitative measurement data related to a prosthetic knee joint installation. In one embodiment, measurement module 180 provides quantitative measurement data related to load magnitude, position of load, position, rotation, tilt, balance, and alignment. In one embodiment, sensors 580 can include one or more inertial sensors for use as a position tracking system. The measurement data from measurement module 180 is used by computer 110 in a kinematic assessment to support installation of prosthetic components to ensure optimal loading, balance, and alignment that improves performance and reliability based on clinical evidence.

Power source 582 provides power to electronic circuitry 390 and sensors 580. The power source 582 can be temporary or permanent. In one embodiment, the power source can be rechargeable. Charging of the power source 582 can comprise wired energy transfer or short-distance wireless energy transfer. A charging power source to recharge power source 582 can include, but is not limited to, a battery or batteries, an alternating current power supply, a radio frequency receiver, an electromagnetic induction coil, a photoelectric cell or cells, a thermocouple or thermocouples, or a transducer energy transfer. In one embodiment, power source 582 has sufficient energy to operate electronic circuitry 390 in measurement module 180 for an orthopedic surgery with a single charge. Furthermore, measurement module 180 can utilize power management technologies to minimize the power drain of power source 582 while in use or when the system is idling.

In one embodiment, power source 582 in measurement module 180 is a battery or a rechargeable battery. The rechargeable battery can be recharged by the methods disclosed herein above. Alternatively, power source 582 can be a super capacitor, an inductor, or other energy storage device. An external charging source can be coupled wirelessly to the rechargeable battery, capacitor, or inductive energy storage device through an electromagnetic induction coil by way of inductive charging. The charging operation can be controlled by power management circuitry 700 within electronic circuitry 390. In one embodiment, power management circuit 700 supports operation of measurement module 180 during charging thereby allowing the surgery to continue if a low charge on power source 582 is detected. For example, power can be transferred to the battery, capacitive energy storage device, or inductive energy storage device by way of efficient step-up and step-down voltage conversion circuitry. This conserves operating power of circuit blocks at a minimum voltage level to support the required level of performance.

Power management circuitry 700 is configured to operate under severe power constraints. In one embodiment, power management circuitry 700 controls power up, power down, and minimizes power usage during operation. The power management circuitry 700 is configured to reduce power dissipation during operation of the system. The power management circuitry 700 can turn off or reduce the power delivered to circuits that are not being used in a specific operation. Similarly, if the system is idle and not being used, the power management circuitry 700 can put other unused circuitry in a sleep mode that awakens prior to the next measurement being made. Power management circuitry 700 can include one or more voltage regulation circuits that provide a plurality of different stable voltages to electronic circuitry 390 and sensors 580.

In one configuration, a charging operation of power source 582 can further serve to communicate downlink data to electronic circuitry. For instance, downlink control data can be modulated onto the energy source signal and thereafter demodulated from an inductor in electronic circuitry 390. This can serve as a more efficient way for receiving downlink data instead of configuring an internal transceiver within electronic circuitry 390 for both uplink and downlink operation. As one example, downlink data can include updated control parameters that measurement module 180 uses when making a measurement, such as external positional information or for recalibration purposes. It can also be used to download a serial number or other identification data.

Control logic 702 controls a measurement process or sequence that engages the sensors, converts the measurement data into a useable format, and transmits the information. Control logic 702 can comprise digital circuitry, a microcontroller, a microprocessor, an ASIC (Application Specific Integrated Circuit), a DSP (Digital Signal Processing), a gate array implementation, a standard cell implementation, and other circuitry. Control logic 702 couples to memory 704. Memory 704 is configured to store measurement data, software routines, diagnostics/test routines, calibration data, calibration algorithms, workflows, and other information or programs. In one embodiment, one or more sensors may be continuously enabled and control logic 702 is configured to receive the measurement data, store the measurement data in memory, or transmit the measurement data. Control logic 702 can include dedicated ports that couple to a sensor to continuously receive measurement data or receive measurement data at different data rates for periodic sampling. Alternatively, control logic 702 can select a sensor to be measured. For example, multiple sensors can be coupled to control logic 702 via a multiplexer. Control logic 702 controls which sensor is coupled through the multiplexer to receive measurement data. Multiplexed measurement data works well when the measurement data is not critical or can be sampled occasionally as needed. Control logic 702 can also select and receive measurement data from different sensors in a sequence. Control logic 702 can be configured to monitor the measurement data from a sensor but transmit measurement data only when a change occurs in the measurement data. Furthermore, control logic 702 can modify the measurement data prior to transmitting the measurement data to computer 110. For example, the measurement data can be corrected for non-linearity using calibration data.

Interface circuitry 706 couples between sensors 580 and control logic 702. Interface circuitry 706 supports conversion of a sensor output to a form that can be received by computer 110. Interface circuitry 706 comprises digital circuitry and analog circuitry. The analog circuitry can include multiplexers, amplifiers, buffers, comparators, filters, passive components, analog to digital converters, and digital to analog converters to name but a few. In one embodiment interface circuitry 706 uses one or more multiplexers to select a sensor for providing measurement data to control logic 702. Control logic 702 is configured to provide control signals that enable the multiplexer to select the sensor for measurement. The multiplexer can be enabled to deliver the measurement data to control logic 702, memory 704, or to be transmitted. Typically, at least one analog to digital conversion or digital to analog conversion of the measurement data occurs via the interface circuitry 706.

Sensors 580 couple through interface circuitry 706 to control logic 702. Alternatively, interface circuitry 706 can couple directly to circuitry for transmitting measurement data as it is measured. The physical parameter or parameters of interest measured by sensors 580 can include, but are not limited to, height, length, width, tilt/slope, position, orientation, load magnitude, force, pressure, contact point location, displacement, density, viscosity, pH, light, color, sound, optical, vascular flow, visual recognition, humidity, alignment, rotation, inertial sensing, turbidity, bone density, fluid viscosity, strain, angular deformity, vibration, torque, elasticity, motion, and temperature. Often, a measured parameter is used in conjunction with another measured parameter to make a kinetic and qualitative assessment. In joint reconstruction, portions of the muscular-skeletal system are prepared to receive prosthetic components. Preparation includes bone cuts or bone shaping to mate with one or more prosthesis. Parameters can be evaluated relative to orientation, alignment, direction, displacement, or position as well as movement, rotation, or acceleration along an axis or combination of axes by wireless sensing modules or devices positioned on or within a body, instrument, appliance, vehicle, equipment, or other physical system.

Sensors 580 can directly or indirectly measure a parameter of interest. For example, a load sensor in measurement module 180 can comprise a capacitor, a piezo sensor, or a MEMs sensor that can compress as loading is applied to the load sensor. Measuring load with a capacitor is an indirect form of sensing as the capacitance value of the capacitor will change with the amount of loading applied to the capacitor. The capacitive measurement data can be sent to computer 110 for further processing. Computer 110 can include software and calibration data related to the elastic capacitors. The load measurement data can be converted from capacitance values to load measurements. Computer 110 can store calibration data that can be used to curve fit and compensate for non-linear output of a sensor over a range of operation. Furthermore, the individual sensor measurement can be combined to produce other measurement data by computer 110. In keeping with the example of load measurement data, the individual load measurement data can be combined or assessed to determine a location where the load is applied to a surface to which the load sensors couple. The measurement data can be displayed on a display that supports a surgeon rapidly assimilating the measurement data. For example, the calculated measurement data on the location of applied load to a surface may have little or no meaning to a surgeon. Conversely, an image of the surface being loaded with a contact point displayed on the surface can be rapidly assimilated by the surgeon to determine if there is an issue with the contact point.

In one embodiment, the orthopedic measurement system transmits and receives information wirelessly. Wireless operation reduces clutter within the surgical area, wired distortion of, or limitations on, measurements caused by the potential for physical interference by, or limitations imposed by, cables connecting a device with an internal power with data collection, storage, or display equipment in an operating room environment. Electronic circuitry 390 includes wireless communication circuitry 720. In one embodiment, wireless communication circuitry 720 is configured for short range telemetry and battery operation. Typically, measurement module 180, and computer 110 are located in an operating room such that the transmission of measurement data from measurement module 180 to computer 110 is less than 10 meters. As illustrated, the exemplary communications system comprises wireless communication circuitry 720 of measurement module 180 and receiving system wireless communication circuitry 722 of computer 110. Wireless communications circuitry 720 comprises, but is not limited to, the antenna 718, a matching network 716, the telemetry transceiver 714, a CRC circuit 712, a data packetizer 710, and a data input 708. Wireless communication circuitry 720 can include more or less than the number of components shown and is not limited to those shown or the order of the components.

Similarly, computer 110 includes wireless communication circuitry 722. Wireless communication circuitry 722 comprises an antenna 724, a matching network 726, a telemetry receiver 728, a CRC circuit 730, and a data packetizer 732. Notably, other interface systems can be directly coupled to the data packetizer 732 for processing and rendering sensor data. In general, electronic circuitry 390 couples to sensors 580 and is configured to transmit quantitative measurement data to computer 110 in real-time to process, display, analyze, and provide feedback. In one embodiment, computer 110 and display 112 is placed just outside the sterile field but in view of the surgical team performing the orthopedic surgery. Measurement module 180 includes a plurality of load sensors located at vertexes of a first polygon on a medial side and a plurality of load sensors at vertexes of a second polygon on a lateral side. In one embodiment, measurement module 180 measures load magnitudes within the area of the first and second polygons as well as outside the first and second polygons. In one embodiment, a contact point respectively within the first polygon on the medial side or the second polygon on lateral side of measurement module over a range of motion is an indication that the joint is performing within normal parameters based on clinical evidence. Conversely, one or more adjustments may be required if the contact point is found to be outside the first or second polygons. The adjustments such as soft tissue tensioning can be performed in real-time such that the contact point is monitored on computer 110 and moved to a desired location on the medial or lateral surface. In one embodiment, measurement module 180 can measure outside the first and second polygons but the measurement accuracy is reduced. In one embodiment, computer 110 can propose a workflow of one or more adjustments such as bone cuts, soft tissue tensioning, shimming, prosthetic component rotation to adjust the loading or contact point (e.g. position of applied load).

A shim of a first type or a second type is coupled to measurement module 180. The shim has a medial articular surface and a lateral articular surface that transfers loading respectively to the medial surface and the lateral surface of measurement module 180 for measurement. In one embodiment, the shim loads measurement module 180 at the vertexes of the first and second polygons. Thus, the first and second polygon translates to the medial articular surface and the lateral articular surface of the shim that is coupled to measurement module 180. Measurement module 180 can further include inertial sensors and other parameter measurement sensors. The measurement data from the plurality of load sensors and the inertial sensors is transmitted to computer 110. Computer 110 can calculate and translate a load magnitude applied to the medial articular surface and the lateral articular surface of the shim and measured by measurement module 180. Computer 110 can further calculate a point of contact on the medial articular surface and the lateral articular surface of the shim coupled to measurement module 180 from the load magnitudes measured at the predetermined locations or vertexes of the polygon on the medial or lateral sides of measurement module 180. Measurement module 180 can further use inertial sensors as a position measurement system or a tracking system. The position or tracking data is also sent to computer 110. The results can also be displayed on display 112 of computer 110. The tracking data can be used to measure the tibia in relation to the femur, A-P slope, M-L slope, alignment, or prosthetic component rotation. In one embodiment, the transmission of the measurement data from different components can be sent on different channels or the measurement data can be sent at different times on the same channel.

As mentioned previously, wireless communication circuitry comprises data input 708, data packetizer 710, crc circuit 712 telemetry transmitter 714, matching network 716, and antenna 718. In general, measurement data from sensors 580 is provided to data input 708 of wireless communication circuitry 720. In one embodiment, the measurement data from sensors 580 can come directly from interface circuitry 706, from memory 704, from control logic 702, or from a combination of paths to data input 708. In one embodiment, measurement data can be stored in memory 704 prior to being provided to data input 708. The data packetizer 710 assembles the measurement data into packets; this includes sensor information received or processed by control logic 702. Control logic 702 can comprise specific modules for efficiently performing core signal processing functions of the measurement module 180. Control logic 702 provides the further benefit of reducing the form factor to meet dimensional requirements for integration into measurement module 180.

The output of data packetizer 710 couples to the input of CRC circuit 712. CRC circuit 712 applies error code detection on the packet data. The cyclic redundancy check is based on an algorithm that computes a checksum for a data stream or packet of any length. These checksums can be used to detect interference or accidental alteration of data during transmission. Cyclic redundancy checks are especially good at detecting errors caused by electrical noise and therefore enable robust protection against improper processing of corrupted data in environments having high levels of electromagnetic activity. The output of CRC circuit 712 couples to the input of telemetry transceiver 714. The telemetry transceiver 714 then transmits the CRC encoded data packet through the matching network 716 by way of the antenna 718. Telemetry transceiver 714 can increase a carrier frequency in one or more steps and add the information or measurement data from measurement module 180 to the carrier frequency. The matching network 716 provides an impedance match for achieving optimal communication power efficiency between telemetry transmitter 714 and antenna 718.

The antenna 718 can be integrated with components of the measurement module 180 to provide the radio frequency transmission. The substrate for the antenna 718 and electrical connections with the electronic circuitry 390 can further include the matching network 716. In one embodiment, the antenna 718 and a portion of the matching network 716 can be formed in or on printed circuit board 488 of FIG. 15 that interconnects the components that comprise electronic circuitry 390. This level of integration of the antenna and electronics enables reductions in the size and cost of wireless equipment. Potential applications may include, but are not limited to any type musculoskeletal equipment or prosthetic components where a compact antenna can be used. This includes disposable modules or devices as well as reusable modules or devices and modules or devices for long-term use. Wireless communication can be on a scientific band, medical band, open communication band, or a low power short range band such as Bluetooth.

The process for receiving wireless communication circuitry 722 is the opposite of the sending process. Antenna 724 receives transmitted measurement data from wireless communication circuitry 720. Wireless communication circuitry 720 can transmit at low power such that receiving wireless communication circuitry 722 must be in proximity, for example within 10 meters to receive measurement data. Antenna 724 couples to matching network 726 that efficiently couples the measurement data to telemetry transmitter circuit 728. The measurement data can be sent on a carrier signal that supports wireless transmission. The measurement data is stripped off from the carrier signal by telemetry transmitter 728. The measurement data is received by CRC circuit 730 from telemetry transmitter 728. CRC circuit 730 performs a cyclic redundancy check algorithm to verify that the measurement data has not been corrupted during transmission. The CRC circuit 730 provides the checked measurement data to data packetizer 732. Data packetizer 732 reassembles the measurement data where it is provided to usb interface 734. USB interface 734 provides the measurement data to computer 110 for further processing.

It should be noted that the measuring, transmitting, receiving, and processing of the measurement data can be performed in real-time for use by a surgeon installing prosthetic join in a surgical environment. In one embodiment, computer 110 displays at least a portion of one prosthetic component. In the example, the medial articular surface and the lateral articular surface of a shim of the first type is displayed on display 112. The medial articular surface includes a polygon 738 on display 112. The lateral articular surface includes a polygon 740 on display 114. As mentioned previously, polygon 738 can differ from polygon 740 by area, contour, or shape. In one embodiment, load sensors underlie the vertexes of polygon 738 and polygon 740 within measurement module 180. In the example, polygons 738 and 740 are drawn as a triangle and shown in display 112. Note that polygons 738 and 740 are a subset or smaller than the medial articular surface or the lateral articular surface of the shim. Polygon 738 can differ in shape, size, or contour from polygon 740. Measurement data from the load sensors is used to calculate a load magnitude and a position of applied load on the medial or lateral surface of the shim. The location of each load sensor is known relative to the medial or lateral articular surfaces of the shim. The position of applied load can be calculated using the location information of each load sensor and the load magnitude at each vertex by computer 110. Similarly, the load magnitude at the position of applied load can be calculated from the load magnitudes at the vertexes of polygon 738 or 740. In the example, a femoral prosthetic component couples to the shim and measurement module in the prosthetic knee joint. The femoral prosthetic component has a medial condyle and a lateral condyle that respectively couples to the medial articular surface and the lateral articular surface of the shim. The medial condyle couples to the shim at contact point 742 as shown on display 112. Similarly, the lateral condyle couples to the shim at contact point 744 as shown on display 112. Medial load magnitude 746 and lateral load magnitude 748 are indicated in display boxes on display 112. The amount of rotation of the shim and measurement module can also be measured with the position measurement system. The amount of rotation is indicated by rotation 736 on display 112. These measurements are measured or calculated in real-time. Adjustments can be performed that affects alignment, loading, position of load, rotation, or other parameters and monitored in real-time on display 112. The adjustments can support optimization after the measured parameters are within specification to fine tune the prosthetic component installation with quantitative measurement data.

Figure 18:
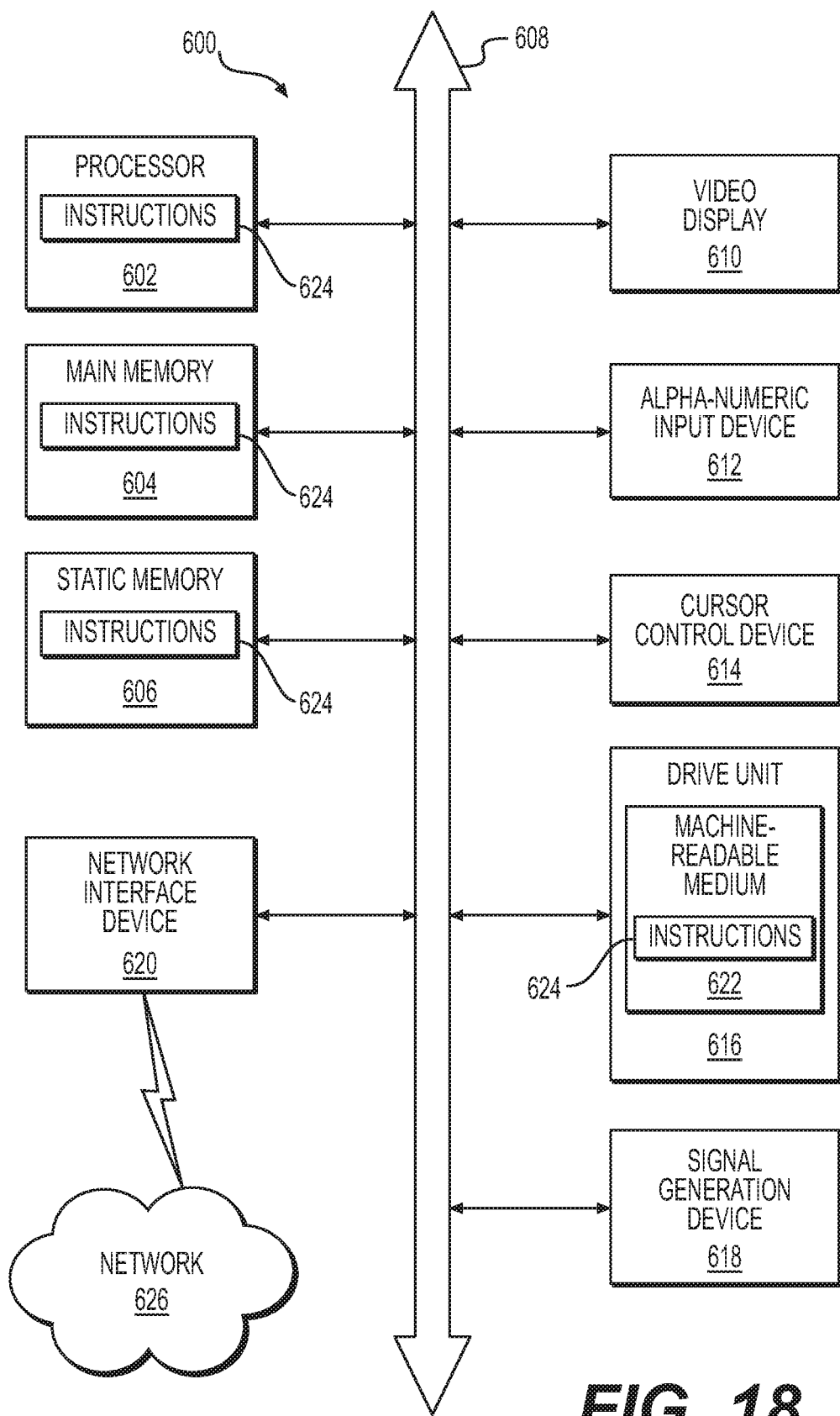
FIG. 18 is a block diagram of a measurement system or computer in accordance with an example embodiment.

FIG. 18 is a block diagram of a measurement system or computer in accordance with an example embodiment. The exemplary diagrammatic representation of a machine, system, or computer in the form of a system 600 within which a set of instructions, when executed, may cause the machine to perform any one or more of the methodologies discussed above. In some embodiments, the machine operates as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a laptop computer, a desktop computer, a control system, logic circuitry, a sensor system, an ASIC, an integrated circuit, a network router, switch or bridge, or any machine capable of executing a set of instructions (sequential or otherwise) that specify actions to be taken by that machine. It will be understood that a device of the present disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methodologies discussed herein.

System 600 may include a processor 602 (e.g., a central processing unit (CPU or DSP), a graphics processing unit (GPU, or both), a main memory 604 and a static memory 606, which communicate with each other via a bus 608. System 600 may further include a video display unit 610 (e.g., a liquid crystal display (LCD), a flat panel, a solid state display, or a cathode ray tube (CRT)). System 600 may include an input device 612 (e.g., a keyboard), a cursor control device 614 (e.g., a mouse), a disk drive unit 616, a signal generation device 618 (e.g., a speaker or remote control) and a network interface device 620.

The disk drive unit 616 can be other types of memory such as flash memory and may include a machine-readable medium 622 on which is stored one or more sets of instructions 624 (e.g., software) embodying any one or more of the methodologies or functions described herein, including those methods illustrated above. Instructions 624 may also reside, completely or at least partially, within the main memory 604, the static memory 606, and/or within the processor 602 during execution thereof by the system 600. Main memory 604 and the processor 602 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine readable medium containing instructions 624, or that which receives and executes instructions 624 from a propagated signal so that a device connected to a network environment 620 can send or receive voice, video or data, and to communicate over the network 626 using the instructions 624. The instructions 624 may further be transmitted or received over the network 626 via the network interface device 620.

While the machine-readable medium 622 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; and carrier wave signals such as a signal embodying computer instructions in a transmission medium; and/or a digital file attachment to e-mail or other self-contained information archive or set of archives is considered a distribution medium equivalent to a tangible storage medium. Accordingly, the disclosure is considered to include any one or more of a machine-readable medium or a distribution medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same functions are considered equivalents.

Figure 19:
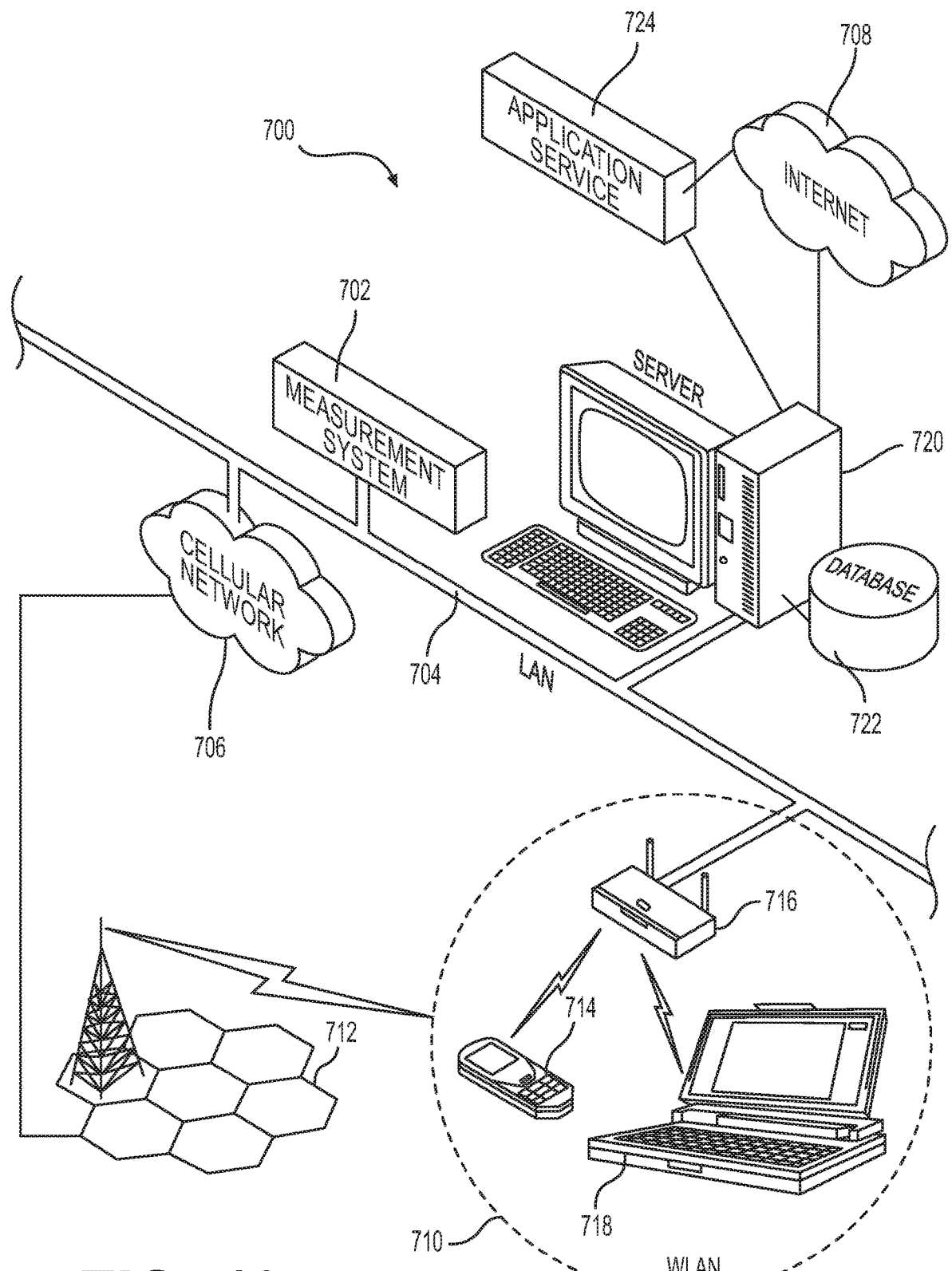
FIG. 19 is an illustration of a communication network for measurement and reporting in accordance with an exemplary embodiment.

FIG. 19 is an illustration of a communication network 700 for measurement and reporting in accordance with an exemplary embodiment. Briefly, the communication network 700 expands broad data connectivity to other devices or services. As illustrated, the measurement and reporting system 702 can be communicatively coupled to the communications network 700 and any associated systems or services. System 702 corresponds to orthopedic measurement system 100 of FIG. 1 configured to measure one or more parameters related to the musculoskeletal system or in proximity to the musculoskeletal system. Communication network 700 supports two-way communication of orthopedic measurement system 100 to another system or database. As one example, measurement system 702 can share its parameters of interest (e.g., angles, load, balance, distance, alignment, displacement, movement, rotation, and acceleration) with remote services or providers, for instance, to analyze or report on surgical status or outcome. This data can be shared for example with a service provider to monitor progress or with plan administrators for surgical monitoring purposes or efficacy studies. The communication network 700 can further be tied to an Electronic Medical Records (EMR) system to implement health information technology practices. In other embodiments, the communication network 700 can be communicatively coupled to HIS Hospital Information System, HIT Hospital Information Technology and HIM Hospital Information Management, EHR Electronic Health Record, CPOE Computerized Physician Order Entry, and CDSS Computerized Decision Support Systems. This provides the ability of different information technology systems and software applications to communicate, to exchange data accurately, effectively, and consistently, and to use the exchanged data.

The communications network 700 can provide wired or wireless connectivity over a Local Area Network (LAN) 704, a Wireless Local Area Network (WLAN) 710, a Cellular Network 706, and/or other radio frequency (RF) system. The LAN 704 and WLAN 710 can be communicatively coupled to the Internet 708, for example, through a central office. The central office can house common network switching equipment for distributing telecommunication services. Telecommunication services can include traditional POTS (Plain Old Telephone Service) and broadband services such as cable, HDTV, DSL, VoIP (Voice over Internet Protocol), IPTV (Internet Protocol Television), Internet services, and so on.

The communication network 700 can utilize common computing and communications technologies to support circuit-switched and/or packet-switched communications. Each of the standards for Internet 708 and other packet switched network transmission (e.g., TCP/IP, UDP/IP, HTML, HTTP, RTP, MMS, SMS) represent examples of the state of the art. Such standards are periodically superseded by faster or more efficient equivalents having essentially the same functions. Accordingly, replacement standards and protocols having the same functions are considered equivalent.

The cellular network 706 can support voice and data services over a number of access technologies such as GSM-GPRS, EDGE, CDMA, UMTS, WiMAX, 2G, 3G, WAP, software defined radio (SDR), and other known technologies. The cellular network 706 can be coupled to base receiver 712 under a frequency-reuse plan for communicating with mobile devices 714.

The base receiver 712, in turn, can connect the mobile device 714 to the Internet 708 over a packet switched link. The internet 708 can support application services 724 and service layers for distributing data from the measurement system 702 to the mobile device 714. Mobile device 714 can also connect to other communication devices through the Internet 708 using a wireless communication channel.

The mobile device 714 can also connect to the Internet 708 over the WLAN 710. Wireless Local Access Networks (WLANs) provide wireless access within a local geographical area. WLANs are typically composed of a cluster of Access Points (APs) 716 also known as base stations. The measurement system 700 can communicate with other WLAN stations such as laptop 718 within the base station area. In typical WLAN implementations, the physical layer uses a variety of technologies such as 802.11ac or 802.11n WLAN technologies. The physical layer may use infrared, frequency hopping spread spectrum in the 2.4 GHz Band, direct sequence spread spectrum in the 2.4 GHz Band, or other access technologies, for example, in the 5.8 GHz ISM band or higher ISM bands (e.g., 24 GHz, etcetera).

By way of the communication network 700, the measurement system 702 can establish connections with a remote server 720 on the network and with other mobile devices for exchanging data. The remote server 720 can have access to a database 722 that is stored locally or remotely and which can contain application specific data. The remote server 720 can also host application services directly, or over the Internet 708.

Figure 20:
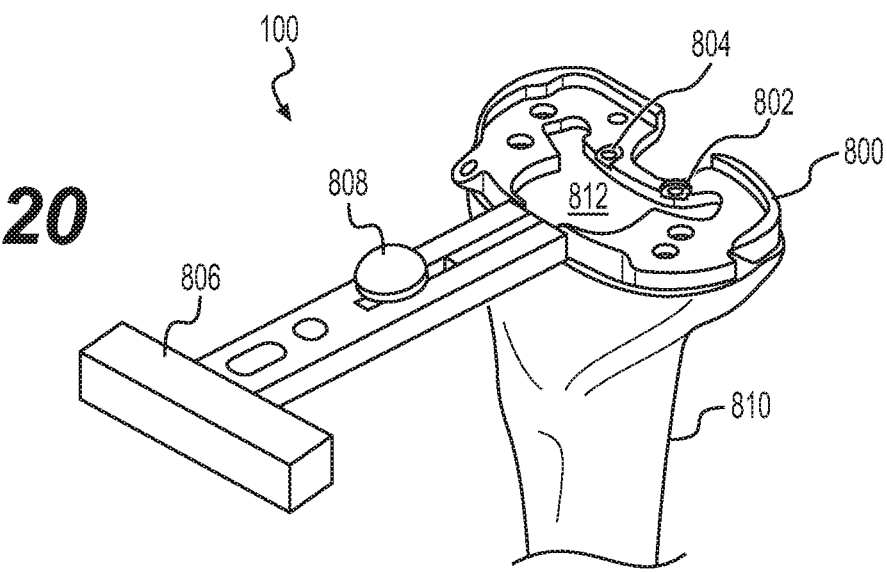
FIG. 20 is an illustration of the orthopedic measurement system including a handle and a tibial prosthetic component in accordance with an example embodiment.

FIG. 20 is an illustration of orthopedic measurement system 100 including a handle and a tibial prosthetic component 800 in accordance with an example embodiment. Tibial prosthetic component 800 is used to support measurement and placement of an insert on a tibia 810. The insert of orthopedic measurement system 100 comprises a shim from plurality of shims 124 or plurality of shims 126 coupled to measurement module 180 of FIG. 1. Tibial prosthetic component 800 is a trialing device that is used before a final tibial prosthetic component is fitted to tibia 810. Tibial prosthetic component 800 has substantially equal dimensions as the final tibial prosthetic component such that a final installation of the final tibial prosthetic component and a final insert will have substantially equal measurement data as generated by measurement module 180 of FIG. 1.

A proximal end of tibia 810 has a prepared bone surface 812. In one embodiment, prepared surface 812 is perpendicular to the mechanical axis of the leg. Alternatively, prepared surface 812 can be prepared having an anterior-posterior slope, a medial-lateral slope, or both. Tibial prosthetic component 800 couples to the prepared bone surface 812. In one embodiment, tibial prosthetic component 800 can be of a first type for a left knee joint or a second type for a right knee joint. In the example, the first and second types are non-symmetrical and can only be used for the designated knee (e.g. left knee or right knee). Tibial prosthetic component 800 can be temporarily retained to prepared surface 812 of tibia 810. In one embodiment, an opening 802 and an opening 804 are formed in tibial prosthetic component 800. A screw or nail can couple through opening 802 or opening 804 into tibia 810 to temporarily retain tibial prosthetic component 800 to prepared surface 812 of tibia 810.

A handle 806 is configured to couple to tibial prosthetic component 800. Handle 806 can be used to place tibial prosthetic component 800 at a reference position on prepared surface 812 of tibia 810. In one embodiment, the reference position can correspond to a rotation of zero degrees relative to the reference position. Handle 806 can also be used to move tibial prosthetic component 800 to a different position. In one embodiment, handle 806 is used to rotate tibial prosthetic component 806 from the reference position. Handle 806 further includes a control 808 that is configured to lock or unlock handle 806 to tibial prosthetic component 800. As mentioned previously, measurement module 180 of FIG. 1 includes a tracking or position measurement system. In one embodiment, the tracking or position measurement system comprises one or more inertial sensors in measurement module 180. The insert comprising the shim coupled to measurement module 180 of FIG. 1 couples to tibial prosthetic component 180. Thus, as tibial prosthetic component 800 is rotated by handle 806 from a reference position, it is measured in real-time by measurement module 180 and sent to computer 110 and displayed on display 112 as shown in FIG. 17. In one embodiment, rotating the insert changes alignment, position of load, and load magnitude on the medial and lateral articular surface of the shim, and position of the insert all of which is quantitatively measured.

Figure 21:
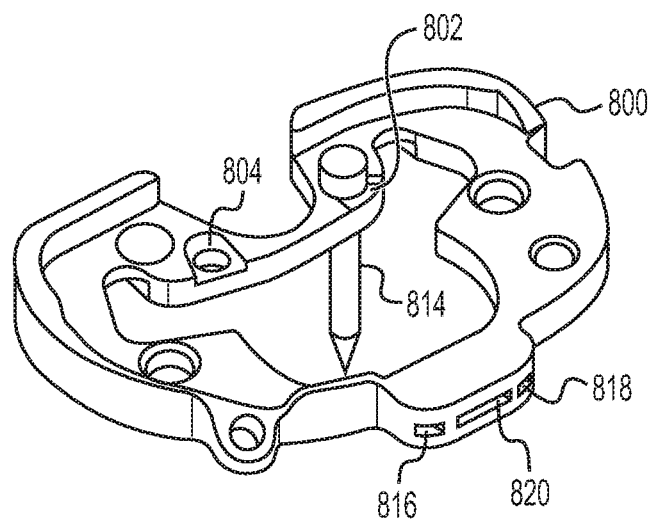
FIG. 21 is an illustration of the tibial prosthetic component in accordance with an example embodiment.

FIG. 21 is an illustration of tibial prosthetic component 800 in accordance with an example embodiment. Tibial prosthetic component 800 includes openings 816 and 818 that couple to handle 806 of FIG. 20. In one embodiment, handle 806 has a first retaining feature and a second retaining feature that is respectively inserted into openings 816 and 818. Tibial prosthetic component 800 further includes an opening 820 configured to lock handle 806 to tibial prosthetic component 800. In one embodiment, a retaining tab locks into opening 820 thereby preventing handle 806 from being separated from tibial prosthetic component 800. Control 808 of FIG. 20 on handle 800 releases the retaining tab from opening 820 thereby allowing handle 806 of FIG. 20 to be removed from tibial prosthetic component 800. As shown, a nail 814 is configured to couple through opening 802 and into tibia 810 of FIG. 20. Nail 814 holds tibial prosthetic component 800 to a tibia but allows tibial prosthetic component 800 to rotate. As mentioned, tibial prosthetic component 800 can be rotated and the amount of rotation measured by measurement module 180 from the reference position to change alignment, position of load or load magnitude for optimization of the knee joint installation. A second nail can be coupled through opening 804 into tibia 810 to fix a position of tibial prosthetic component 800 and the insert for further measurement or adjustment. In one embodiment, the openings formed by nail 814 and the second nail in prepared surface 812 of FIG. 20 are used to align a final tibial prosthetic component 800 to tibia 810 in the same position as tibial prosthetic component 800.

Figure 22:
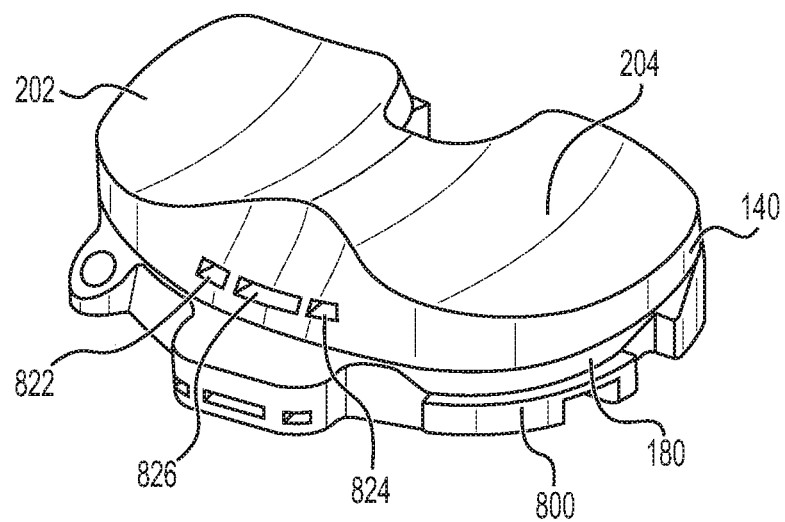
FIG. 22 is an illustration of the insert of FIG. 2 coupled to the tibial prosthetic component in accordance with an example embodiment.

FIG. 22 is an illustration of an insert coupled to tibial prosthetic component 800 in accordance with an example embodiment. In the example, the insert comprises shim 140 of a first type of plurality of shims 124 coupled to a first side of measurement module 180 briefly referring to FIGS. 2 and 3. Shim 140 has medial articular surface 202 and lateral articular surface 204. The second side of measurement module 180 couples to and is retained by tibial prosthetic component 800. Each shim of the plurality of shims can be used to couple to the first side of measurement module 180 to yield an insert of a different height. In one embodiment, the first side or the second side of measurement module 180 can couple to tibial prosthetic component 180.

Alternatively, a second tibial prosthetic component can be provided with the system for an insert comprising a shim of the second type coupled to the second side of measurement module 180. The first side of measurement module 180 couples to the second tibial prosthetic component. In one embodiment, the first tibial prosthetic component 800 couples to a left tibia and the second tibial prosthetic component couples to the right tibia. Shim 140 further comprises openings 822 and 824. Referring briefly to FIG. 20, handle 806 can couple to openings 822 and 824 that are similar to openings 816 and 818 of FIG. 21. Similarly, the retaining tab of handle 806 can lock into opening 826 of shim 140 to retain handle 806 shim 140. Handle 806 can be used to place or move the insert. Each shim of plurality of shims 124 and plurality of shims 126 of FIG. 1 has similar openings to 822, 824, and 826 to support coupling of handle 806 to each shim or insert.

Referring briefly to FIGS. 1, 2, 4, 7, 10, and 15 a shim of a first type couples to measurement module 180. The first type corresponds to one or more prosthetic components or parts for prosthetic components for a left leg or left knee joint. In one embodiment, parts of the first type cannot be used on a right leg or right knee joint. Shim 140 has a first plurality of columns and a second plurality of columns respectively coupled to medial surface 202 and lateral surface 204 of shim 140. The first plurality of columns and the second plurality of columns respectively couple to medial surface 182 and lateral surface 184 of measurement module 180. In one embodiment, medial surface 182 and lateral surface 184 correspond to a first side of measurement module 180. Shim 140 is an example of how a shim of plurality of shims 124 couples to measurement module 180 to measure loading and position of load. As mentioned previously, shim 140 is 16 millimeter shim from plurality of shims 124. In one embodiment, shim 140 comprises columns 240, 242, and 244 on the medial side and columns 234, 236, and 238 on the lateral side of shim 140. Measurement module 180 is configured to measure loading applied to medial articular surface 202 and lateral articular surface 204 of shim 140 when coupled together. In one embodiment, medial surface 182 on a first side of measurement module 180 differs in area, contour, or shape from lateral surface 184 on the first side of measurement module 180. In one embodiment, medial articular surface 202 differs in area, contour, or shape than lateral articular surface 204 of shim 140. In one embodiment, load sensors 400, 402, and 404 of measurement module 180 are configured to be respectively aligned to and underlie columns 244, 242, and 240 of shim 140 when the first side of measurement module 180 couples to shim 140. Similarly, load sensors 410, 412, and 414 are configured to be respectively aligned to and underlie columns 238, 236, and 234 of shim 140 when the first side of measurement module 180 couples to shim 140. Load sensors 400, 402, 404, 410, 412, and 414 can be a capacitor, a piezo sensor, or a MEMs sensor formed in the interconnect or coupled to the interconnect.

Referring briefly to FIGS. 1, 2, 4, 11, and 16 a shim of a second type couples to measurement module 180. The second type corresponds to one or more prosthetic components or parts for prosthetic components for a right leg or right knee joint. In one embodiment, the shim of the second type cannot be used on a left leg or left knee joint. Shim 160 has a first plurality of columns and a second plurality of columns respectively coupled to medial surface 210 and lateral surface 212 of shim 160. The first plurality of columns and the second plurality of columns of shim 160 respectively couple to medial surface 186 and lateral surface 188 of measurement module 180. In one embodiment, medial surface 186 and lateral surface 188 correspond to a second side of measurement module 180. Shim 160 is an example of how a shim of plurality of shims 126 couples to measurement module 180. As mentioned previously, shim 160 is 16 millimeter shim from plurality of shims 126. In one embodiment, shim 160 comprises columns 540, 542, and 544 on the medial side and columns 550, 552, and 554 on the lateral side of shim 160. Measurement module 180 is configured to measure loading applied to medial articular surface 210 and lateral articular surface 212 of shim 160 when coupled together. The position of load or contact point can be measured from the measurement data using the predetermined locations of columns 540, 542, 544, 550, 552, and 554 relative to medial surface 210 and lateral surface 212. In one embodiment, medial surface 186 on a second side of measurement module 180 differs in area, contour, or shape from lateral surface 188 on the second side of measurement module 180. In one embodiment, medial articular surface 210 differs in area, contour, or shape than lateral articular surface 212 of shim 160. In one embodiment, load sensors 400, 402, and 404 of measurement module 180 are configured to be respectively aligned to and underlie columns 540, 542, and 544 of shim 160 when the second side of measurement module 180 couples to shim 160. Similarly, load sensors 410, 412, and 414 are configured to be respectively aligned to and underlie columns 550, 552, and 554 of shim 160 when the second side of measurement module 180 couples to shim 160.

Referring briefly to FIGS. 12 and 15, at least three load sensors are coupled between medial surface 182 and medial surface 186 of measurement module 180. In the example, load sensors 400, 402, and 404 couple between medial surface 182 and medial surface 186 of measurement module 180. Load sensors 400, 402, and 404 are placed at vertexes of a first triangle. Similarly, at least three load sensors are coupled between lateral surface 184 and lateral surface 188 of measurement module 180. In the example, load sensors 410, 412, and 414 couple between lateral surface 184 and lateral surface 188 of measurement module 180. Load sensors 410, 412, and 414 are placed at vertexes of a second triangle. The exact position of each load sensor is known within measurement module 180, relative to medial surfaces 182 and 186, relative to lateral surfaces 184 and 188, and relative to the medial and lateral articular surfaces of any shim from shims 124 and shims 126. The position data of the each load sensor is provided to computer 110 to support calculation of the position of load or contact point. The first and second triangles correspond to the location of the load sensors on the medial or lateral sides of measurement module 180 and can differ in shape and area. Electronic circuitry 390 couples to the at least three load sensors coupled between medial surface 182 and medial surface 186. In the example, interconnect 394 couples load sensors 400, 402, and 404 to electronic circuitry 390. Similarly, electronic circuitry 390 couples to the at least three load sensors coupled between lateral surface 184 and lateral surface 188. In the example, interconnect 392 couples load sensors 410, 412, and 414 to electronic circuitry 390. Electronic circuitry 390 can be mounted on a printed circuit board 488. Electronic circuitry 390 and load sensors 400, 402, 404, 410, 412, and 414 are hermetically sealed from an external environment when support structure 340 and support 342 are coupled together. Electronic circuitry 390 supports a measurement process and transmits measurement data to a computer. The computer can have a display to provide the measurement data in real-time.

Electronic circuitry 390 is powered by power source 494 and power source 496. Power sources 494 and 496 respectively underlie at least a portion of medial surface 182 and at least a portion of lateral surface 184. In one embodiment, power sources 494 and 496 are not under compression when measurement module 180 is under load. In one embodiment, at least a portion of power source 494 couples between medial surface 182 of support structure 340 and medial surface 186 of support structure 342. In one embodiment, at least a portion of power source 496 couples between lateral surface 184 of support structure 340 and lateral surface 188 of support structure 342 Interconnect 398 couples power source 494 to electronic circuitry 390. In one embodiment, interconnect 398 couples to printed circuit board 488. Interconnect 396 couples power source 496 to electronic circuitry 390. In one embodiment, interconnect 396 couples to printed circuit board 488. Measurement module 180 can be used in a surgical environment. Power sources 494 and 496 have sufficient power to enable electronic circuitry 390 for an extended surgery such as a joint installation.

Referring to FIGS. 1, 2, 3, 12, and 15 a plurality of shims 124 of a first type and a plurality of shims 126 of a second type are provided with the knee measurement system. In one embodiment, plurality of shims 124 of the first type are for a left leg or left knee joint and plurality of shims 126 of the second type are for a right leg or right knee joint. Each shim of plurality of shims 124 and plurality of shims 126 has a medial articular surface and a lateral articular surface. As mentioned previously, plurality of shims 124 cannot be used on a right knee joint and plurality of shims 126 cannot be used on a left knee joint. Each shim of plurality of shims 124 is non-symmetrical about the anterior-posterior axis. Each shim of plurality of shims 126 is non-symmetrical about the anterior-posterior axis. In general, the medial articular surface differs from the lateral articular surface of a shim in area, contour, or shape. Each shim of plurality of shims 124 and 126 have a plurality of columns extending from a medial articular surface and a plurality of columns extending from a lateral articular surface similar to that disclosed for shim 140 and shim 160 herein above. The position or location of the plurality of columns coupled to the medial articular surface or the lateral articular surface of each shim is known and correspond to vertexes of a polygon as disclosed herein above. Each column of the plurality of columns coupled to the medial articular surface or the lateral articular surface of each shim are configured to couple to corresponding sensor located in measurement module 180.

Measurement module 180 has medial surface 182 and lateral surface 184 on a first side. Measurement module 180 has a medial surface 186 and a lateral surface 188 on a second side. Each shim of plurality of shims 124 couples to the first side of measurement module 180. Each shim of plurality of shims 126 couples to the second side of measurement module 180. Load sensors are placed at vertexes of a first polygon on a medial side of measurement module 180. Load sensors are placed at vertexes of a second polygon on a lateral side of measurement module 180. In one embodiment, the first polygon defines an area of measurement on the medial side of measurement module 180 and on a medial articular surface of a shim coupled to measurement module 180. In one embodiment, the second polygon defines an area of measurement on the lateral side of measurement module 180 and on a lateral articular surface of the shim coupled to measurement module 180. Measurement data from each load sensor on the medial side and the lateral side of measurement module 180 is sent by wire or wireless transmission. In the example, the shim and measurement module 180 is used in an operating room to provide measurement data on a knee joint application. Computer 110 having display 112 is configured to receive the measurement data from measurement module 180 wirelessly in real-time and to display the measurement data within the surgical environment for a surgical team. The computer uses the measurement data to determine the load magnitude applied to the medial articular surface of the shim and the load magnitude applied to the lateral articular surface of the shim when coupled to measurement module 180 and placed in the prosthetic knee joint. The computer can further identify the point of contact on the medial articular surface of the shim and the lateral articular surface of the shim. Measurement module 180 can further include a tracking system to monitor position, location, movement, rotation, angle, or slope. In one embodiment, the tracking system can comprise one or more inertial sensors configured to track position or location on at least one prosthetic component of the prosthetic knee joint. Measurement module 180 can further support real-time change in the prosthetic knee joint with quantitative measurement. For example, soft tissue tensioning can be used to change load or position of load on the medial or lateral articular surface of the shim in real-time. Computer 110 and display 112 can display changes as the tissue is cut. Similarly, prosthetic components can be rotated or bone cuts can be made that changes prosthetic component orientation, loading, and position of load. The amount of rotation, change in slope, or position of the prosthetic components can be monitored in real-time.

Referring briefly to FIGS. 1, 12, and 15, measurement module 180 includes a first sensor, a second sensor, a third sensor, a fourth sensor, a fifth sensor, and a sixth sensor respectively corresponding to load sensors 400, 402, 404, 410, 412, and 414. In one embodiment load sensors 400, 402, 404, 410, 412, and 414 are capacitors, MEMs load sensors, piezo load sensors, strain gauges, or other sensor types that meet the form factor for a prosthetic component. Load sensors 400, 402, and 404 are placed at a first vertex, a second vertex, and a third vertex of a first triangle. Load sensors 400, 402, and 404 are placed between medial surface 182 and medial surface 186 of measurement module 180. Similarly, load sensors 410, 412, and 414 are respectively placed at a fourth vertex, fifth vertex, and a sixth vertex of a second triangle. Load sensors 410, 412, and 414 are placed between lateral surface 184 and 188 of measurement module 180 at the vertexes. Medial surface 182 and lateral surface 184 is on a first side of measurement module 180. Medial surface 186 and lateral surface 188 is on a second side or measurement module 180. In one embodiment, the first triangle differs from the second triangle in area, contour, or shape.

Electronic circuitry 390 is coupled to the first, second, third, fourth, fifth, and six sensors and is configured to control a measurement process and transmit measurement data. In one embodiment, sensor 410 In one embodiment, load sensors 400, 402, and 404 couple to electronic circuitry 390 by interconnect 394. In one embodiment, load sensors 410, 412, and 414 couple to electronic circuitry 390 by interconnect 392. Measurement module 180 includes at least a power source 494 and a power source 496. Power source 494 and 496 respectively couple to electronic circuitry 390 by interconnect 398 and interconnect 396. Interconnect 392, 394, 396, and 398 can be flexible interconnect. At least a portion of power source 494 resides within a region defined by the first triangle on the medial side of measurement module 180. Similarly, at least a portion of power source 496 resides within a region of the second triangle on the lateral side of measurement module 180. In one embodiment, measurement module 180 does not compress power source 494 or power source 496 when under load by the prosthetic knee joint. In one embodiment, power source 494 and 496 are batteries capable of powering measurement module 180 during a prosthetic joint installation. In one embodiment, measurement module 180 is disposed of after a prosthetic joint installation and cannot be used again.

Referring briefly to FIGS. 1, 2, 7, 10, 11, 12, 13, 14, 15, and 16 measurement module 180 comprises a support structure 340 having exterior medial surface 182 and exterior lateral surface 184. Exterior medial surface 182 of support structure 340 has raised regions 350, 352, and 354 respectively located at vertexes of a first polygon on exterior medial surface 182. Exterior lateral surface 184 has raised regions 360, 362, and 364 located at vertexes of a second polygon on the exterior lateral surface 184. In one embodiment, the first polygon differs from the second polygon by area, shape, or contour. Peripheral raised region 370 on a medial side of support structure 340 couples to raised regions 350, 352, and 354. Similarly, peripheral raised region 372 couples to raised regions 360, 362, and 364. In one embodiment, loading applied to a shim coupled to support structure 340 of measurement module 180 couples through raised regions 350, 352, and 354 on the medial side and raised regions 360, 362, and 364 on a lateral side. In one embodiment medial surface 182 and lateral surface 184 is not loaded other than through the raised regions. In one embodiment, peripheral raised regions 370 and 372 respectively strengthen raised regions 340, 352, and 354 and raised regions 360, 362, and 364 under load compression. In one embodiment, raised regions 340, 352, 354, 360, 362, and 364 comprise more material than the non-raised regions of medial surface 182 and lateral surface 184 of support structure 340.

Measurement module 180 further comprises a support structure 342 having exterior medial surface 186 and exterior lateral surface 188. Exterior medial surface 186 of support structure 342 has raised regions 370, 372, and 374 respectively located at vertexes of the first polygon on exterior medial surface 186. Exterior lateral surface 188 of support structure 342 has raised regions 380, 382, and 384 located at vertexes of the second polygon on the exterior lateral surface 188. Thus, raised regions 350, 352, and 354 are respectively aligned to raised regions 370, 372, and 374 corresponding to vertexes of the first polygon. Similarly, raised regions 360, 362, and 364 are respectively aligned to raised regions 380, 382, and 384 corresponding to vertexes of the second polygon. In one embodiment, loading applied to a shim coupled to support structure 342 of measurement module 180 couples through raised regions 370, 372, and 374 on the medial side and raised regions 380, 382, and 384 on a lateral side. In one embodiment medial surface 186 and lateral surface 187 is not loaded other than at the raised regions. In one embodiment, peripheral raised regions 390 and 392 respectively strengthen raised regions 370, 372, and 374 and raised regions 380, 382, and 384 under load compression. In one embodiment, raised regions 370, 372, 374, 380, 382, and 384 comprise more material than the non-raised regions of medial surface 186 and lateral surface 188 of support structure 342.

Support structures 340 and 342 couple together to form a housing. In one embodiment, the housing is hermetically sealed. In on embodiment, support structures 340 and 342 can comprise a polymer material, a metal, an alloy, or a composite material. Support structures 340 and 342 can be molded, machined, formed, or printed. In one embodiment, support structure 340 has tongue 426 and support structure 342 has glue channel 456. The tongue of support structure 340 fits into the glue channel 456. An adhesive is placed in glue channel 456 to adhere tongue 426 to glue channel 456 thereby hermetically sealing support structure 340 to support structure 342. The housing houses a first plurality of load sensors and a second plurality of load sensors configured to respectively measure a load applied to a medial side and a lateral side of measurement module 180. As disclosed herein above, first side 194 of measurement module 180 is configured to couple to a shim of a first type from plurality of shims 124. Second side 196 of measurement module 180 is configured to couple to a shim of a second from plurality of shims 126. The first plurality of load sensors couple between exterior medial surfaces 182 and 186. In one embodiment, load sensors 400, 402, and 404 underlie raised regions 350, 352, and 354 of support structure 342 within the housing. Load sensors 400, 402, and 404 respectively couple between raised regions 350, 352, and 354 and raised regions 370, 372, and 374 on the medial side of measurement module 180. The second plurality of load sensors couple between exterior lateral surfaces 184 and 188. In one embodiment, load sensors 410, 412, and 414 respectively underlie raised regions 360, 362, and 364 of support structure 342 within the housing. Load sensors 410, 412, and 414 respectively couple between raised regions 360, 362, and 364 and raised regions 380, 382, and 384 on the lateral side of measurement module 180. Electronic circuitry couples to sensors 400, 402, 404, 410, 412, and 414 to control a measurement process and transmits measurement data. Computer 110 is configured to receive the measurement data and display the measurement data.

In general, measurement module 180 is a non-symmetric shape. In one embodiment, measurement module 180 is non-symmetrical about the anterior-posterior (A-P) axis. Exterior medial surface 182 and exterior lateral surface 184 of support structure 340 can differ in area, shape, or contour. Similarly, exterior medial surface 186 and exterior lateral surface 188 of support structure 342 can differ in area, shape, or contour. In one embodiment, the area, shape, and contour of exterior medial surface 182 of support structure 340 is identical to the area, shape, or contour of exterior medial surface 186 of support structure 342. In one embodiment, the area, shape, or contour of exterior lateral surface 184 of support structure 340 is identical to the area, shape, or contour of exterior lateral surface 188 of support structure 342. In one embodiment, each shim of plurality of shims 124 is non-symmetrical about the A-P axis. Similarly, each shim of plurality of shims 126 is non-symmetrical about the A-P axis.

Electronic circuitry 390 is placed between the medial side and the lateral side of measurement module 180. Electronic circuitry can be mounted and interconnected on a printed circuit board. Electronic circuitry 390 are not compressed or loaded by the femoral prosthetic component. Load sensors 400, 402, and 404 on the medial side of measurement module couple to electronic circuitry 390 by interconnect 394. Load sensors 410, 412, and 414 on the lateral side of measurement module 180 couple to electronic circuitry by interconnect 392. Interconnect 392 and 394 can have multiple layers of interconnect and can be flexible. In one embodiment, load sensors 400, 402, and 404 are integrated into interconnect 394. Similarly, load sensors 410, 412, and 414 can be integrated into interconnect 392. Alternatively, the load sensors can be coupled to interconnect 392 and 394. The load sensors can comprise MEMs devices, strain gauges, piezo-devices, or capacitors.

Electronic circuitry 390 receives power from power source 494 and power source 496. Power source 494 and power source 496 are respectively placed on the medial side and the lateral side of measurement module 180. A portion of power source 494 couples between the exterior medial surface 182 and exterior medial surface 186 respectively of support structure 340 and support structure 342 of measurement module 180. A portion of power source 496 couples between exterior lateral surface 184 and exterior lateral surface 188 respectively of support structure 340 and support structure 342 of measurement module 180. Measurement module 180 is configured to not to load power source 494 or power source 496 under compression in a prosthetic knee joint.

In one embodiment, a shim can be selected from plurality of shims 124 to couple to measurement module 180. The plurality of shims 124 are of a first type and are configured to couple to first side 194 of measurement module 180. In one embodiment, the first type corresponds to prosthetic components used for a left leg or left knee joint. Shim 140 of plurality of shims 124 includes medial side columns 244, 242, and 240 and lateral side columns 238, 236, and 234 configured to respectively couple to medial side raised regions 350, 352, and 354 and lateral side raised regions 360, 362, and 364. Each shim of plurality of shims 124 differs in height but have the same number of columns on the medial or the lateral sides that couple to the same locations on the first side 194 of measurement module 180. Columns 244, 242, and 240 of shim 140 couple to medial articular surface 202 of shim 140 at vertexes of the first polygon. Columns 238, 236, and 234 couple to lateral articular surface 204 of shim 140 at vertexes of the second polygon. In the example the first and second polygons are triangles.

In one embodiment, a shim can be selected from plurality of shims 126 to couple to measurement module 180. The plurality of shims 126 are of a second type and are configured to couple to second side 196 of measurement module 180. In one embodiment, the second type corresponds to prosthetic components used for a right leg or right knee joint. Shim 160 of plurality of shims 126 includes medial side columns 540, 542, and 544 and lateral side columns 550, 552, and 554 configured to respectively couple to medial side raised regions 370, 372, and 374 and lateral side raised regions 380, 382, and 384. Each shim of plurality of shims 126 differs in height but have the same number of columns on the medial or the lateral sides that couple to the same locations on the second side 196 of measurement module 180. Columns 380, 382, and 384 of shim 160 couple to medial articular surface 210 of shim 160 at vertexes of the first polygon. Columns 550, 552, and 554 couple to lateral articular surface 212 of shim 160 at vertexes of the second polygon.

In one embodiment, first support structure 340 includes medial side raised regions 420, 422, and 424 and lateral side raised regions 430, 432, and 434 respectively on interior medial surface 438 and interior lateral surface 440. Raised regions 420, 422, and 424 of support structure 340 couple to vertexes of the first polygon and align with raised regions 350, 352, and 354. Raised regions 430, 432, and 434 of support structure 340 couple to vertexes of the second polygon and align with raised regions 360, 362, and 364. Similarly, second support structure 342 includes medial side raise regions 450, 452, and 454 and lateral side raised regions 460, 462, and 464 respectively on interior medial surface 490 and interior lateral surface 492. Raised regions 450, 452, and 454 of support structure 342 couple to vertexes of the first polygon and align with raised regions 370, 372, and 374. Raised regions 460, 462, and 464 of support structure 342 couple to vertexes of the second polygon and align with raised regions 380, 382, and 384. The internal raised regions further increase the material located at vertexes of the first or second polygon to strengthen areas receiving loading.

It should be noted that very little data exists on implanted orthopedic devices. Most of the data is empirically obtained by analyzing orthopedic devices that have been used in a human subject or simulated use. Wear patterns, material issues, and failure mechanisms are studied. Although, information can be garnered through this type of study it does yield substantive data about the initial installation, post-operative use, and long term use from a measurement perspective. Just as each person is different, each device installation is different having variations in initial loading, balance, and alignment. Having measured data and using the data to install an orthopedic device will greatly increase the consistency of the implant procedure thereby reducing rework and maximizing the life of the device. In at least one exemplary embodiment, the measured data can be collected to a database where it can be stored and analyzed. For example, once a relevant sample of the measured data is collected, it can be used to define optimal initial measured settings, geometries, and alignments for maximizing the life and usability of an implanted orthopedic device.

The present invention is applicable to a wide range of medical and nonmedical applications including, but not limited to, frequency compensation; control of, or alarms for, physical systems; or monitoring or measuring physical parameters of interest. The level of accuracy and repeatability attainable in a highly compact sensing module or device may be applicable to many medical applications monitoring or measuring physiological parameters throughout the human body including, not limited to, bone density, movement, viscosity, and pressure of various fluids, localized temperature, etc. with applications in the vascular, lymph, respiratory, digestive system, muscles, bones, and joints, other soft tissue areas, and interstitial fluids.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the invention.

What is claimed is:

1. A knee measurement system comprising:
    a first shim of a first type having a medial articular surface and a lateral articular surface wherein the first shim is non-symmetrical about the anterior-posterior axis;
    a second shim of a second type having a medial articular surface and a lateral articular surface wherein the second shim is non-symmetrical about an anterior-posterior axis;
    a measurement module having a first medial surface and a first lateral surface on a first side of the measurement module and a second medial surface and a second lateral surface on a second side of the measurement module wherein the measurement module is configured to measure loading applied to the first shim or the second shim when installed in a knee joint, wherein the first side of the measurement module is configured to couple to the first shim, and wherein the second side of the measurement module is configured to couple to the second shim; and
    a tibial prosthetic component wherein a handle is configured to couple to the tibial prosthetic component to support movement of the tibial prosthetic component and wherein the handle is configured to couple to the first or second shim.

2. The knee measurement system of claim 1 further including a first plurality of shims of the first type wherein each of the first plurality of shims have a different height.

3. The knee measurement system of claim 1 further including a second plurality of shims of the second type wherein each of the second plurality of shims have a different height.

4. The knee measurement system of claim 1 wherein the first medial surface and first lateral surface of the measurement module are non-symmetrical about the anterior-posterior axis.

5. The knee measurement system of claim 1 wherein the first medial surface of the measurement module differs in area or contour from the first lateral surface of the measurement module.

6. The knee measurement system of claim 1 wherein the measurement module includes:
    at least three load sensors coupled between the first medial surface and the second medial surface of the measurement module;
    at least three load sensors coupled between the first lateral surface and the second lateral surface of the measurement module; and
    electronic circuitry coupled to the at least three load sensors coupled between the first medial surface and the second medial surface of the measurement module and the at least three load sensors coupled between the first lateral surface and the second lateral surface of the measurement module.

7. The knee measurement system of claim 6 wherein the at least three load sensors coupled to the first and second medial surfaces are placed at vertexes of a first polygon, wherein the at least three load sensors coupled to the first lateral surface or the second lateral surface are placed at vertexes of a second polygon, and wherein the first polygon differs in area from the second polygon.

8. The knee measurement system of claim 6 further including a computer wherein the electronic circuitry of the measurement module is configured to control a measurement process and transmit measurement data to the computer.

9. The knee measurement system of claim 6 further including:
- a first power source underlying the first medial surface of the measurement module; and
- a second power source underlying the first lateral surface of the measurement module wherein the first and second power source couple to the electronic circuitry and wherein the first and second power source are configured to power the measurement module during a knee joint installation.

10. The knee measurement system of claim 1 wherein the measurement module is non-symmetrical about the anterior-posterior axis.

11. A knee measurement system comprising:
- a first plurality of shims of a first type each having a medial articular surface and a lateral articular surface wherein each of the first plurality of shims is non-symmetrical about an anterior-posterior axis;
- a second plurality of shims of a second type each having a medial articular surface and a lateral articular surface wherein each of the second plurality of shims is non-symmetrical about the anterior-posterior axis;
- a measurement module having a first medial surface and a first lateral surface on a first side of the measurement module and a second medial surface and a second lateral surface on a second side of the measurement module wherein the measurement module is configured to measure loading applied to a first shim of the first plurality of shims when the first shim is coupled to the first side of the measurement module, or wherein the measurement module is configured to measure loading applied to a second shim of the second plurality of shims when the second shim is coupled to the second side of the measurement module;
- electronic circuitry configured to control a measurement process and transmit measurement data wherein the electronic circuitry couples to three or more sensors coupled between the first medial surface and the second medial surface of the measurement module and wherein the electronic circuitry couples to three or more sensors coupled between the first lateral surface and the second lateral surface of the measurement module;
- a first power source coupled to the electronic circuitry wherein at least a portion of the first power source resides between the first medial surface and the second medial surface; and
- a second power source coupled to the electronic circuitry wherein at least a portion of the second power source resides between the first lateral surface and the second lateral surface.

12. The knee measurement system of claim 11 wherein the three or more sensors between the first medial surface and the second medial surface of the measurement module are placed at vertexes of a first polygon and wherein the three or more sensors between the first lateral surface and the second lateral surface of the measurement module are placed at vertexes of a second polygon.

13. The knee measurement system of claim 12 further including a computer and a display wherein the computer is configured to receive measurement data from the measurement module and wherein the display is configured to display the measurement data.

14. The knee measurement system of claim 11 wherein the measurement module is non-symmetrical about the anterior-posterior axis.

15. The knee measurement system of claim 11 further including a tibial prosthetic component configured to couple to a tibia wherein the measurement module couples to the tibial prosthetic component, wherein a handle is configured to couple to the tibial prosthetic component to rotate the tibial prosthetic component from a reference position, and wherein the handle is configured to couple to the first plurality of shims or the second plurality of shims.

16. A knee measurement system comprising:
- a shim of a first plurality of shims wherein the shim has a medial surface and a lateral surface and wherein at least one column couples to the medial surface or the lateral surface at a predetermined location of the shim;
- a measurement module having a first medial surface and a first lateral surface on a first side of the measurement module and a second medial surface and a second lateral surface on a second side of the measurement module, wherein the shim couples to the first side of the measurement module, wherein the measurement module is configured to measure loading applied to the shim when installed in a knee joint, and wherein the at least one column of the shim couples the predetermined location on the medial surface or the lateral surface of the shim to a load sensor in the measurement module; and
- a computer configured to receive measurement data from the measurement module wherein the computer is coupled to a display configured to display the measurement data, and wherein the computer uses the predetermined location on the medial or lateral surface of the shim to calculate a position of applied load on the medial surface or the lateral surface of the shim.

17. The knee measurement system of claim 16 wherein the computer uses the predetermined location of the medial or lateral surface of the shim in a calculation of a position of applied load to the medial or lateral surface of the shim.

18. The knee measurement system of claim 17 wherein the computer uses the predetermined location of the medial or lateral surface of the shim in a calculation of a load magnitude at the position of applied load to the medial or lateral surface of the shim.

19. The knee measurement system of claim 16 wherein the measurement module includes electronic circuitry configured to control a measurement process and transmit measurement data wherein the load sensor in the measurement module is a strain gauge.

20. The knee measurement system of claim 16 further including a shim of a second type from a second plurality of shims wherein the shim of the second type has a medial surface and a lateral surface, wherein at least one column of the shim of the second type couples to the medial surface or the lateral surface at a predetermined location of the shim of the second type, wherein the shim of the second type is configured to couple to the second side of the measurement module, and wherein the at least one column of the shim of the second type couples the predetermined location on the medial surface or the lateral surface of the shim of the second type to the load sensor in the measurement module.

\* \* \* \* \*